United States Patent [19]
Lethe et al.

[11] Patent Number: 5,744,316
[45] Date of Patent: Apr. 28, 1998

[54] ISOLATED, TYROSINASE DERIVED PEPTIDES AND USES THEREOF

[75] Inventors: Bernard Lethe; Vincent Brichard; Aline Van Pel, all of Brussels; Thomas Wölfel, Mainz; Thierry Boon-Falleur, Brussels, all of Belgium

[73] Assignee: Ludwig Institute for Cancer Research, New York, N.Y.

[21] Appl. No.: 587,391

[22] Filed: Jan. 17, 1996

Related U.S. Application Data

[63] Continuation-in-part of Ser. No. 233,305, Apr. 26, 1994, Pat. No. 5,519,117, which is a continuation-in-part of Ser. No. 203,054, Feb. 28, 1994, Pat. No. 5,530,096, which is a continuation-in-part of Ser. No. 81,673, Jun. 23, 1993, Pat. No. 5,487,974, which is a continuation-in-part of Ser. No. 54,714, Apr. 28, 1993, which is a continuation-in-part of Ser. No. 994,928, Dec. 22, 1992, abandoned.

[51] Int. Cl.$^6$ ............... G01N 33/53; A61K 39/385; A61K 38/04
[52] U.S. Cl. ............... 435/7.24; 424/193.1; 530/328
[58] Field of Search ............... 435/7.24; 424/193.1; 530/328

[56] References Cited

U.S. PATENT DOCUMENTS

| | | | |
|---|---|---|---|
| 4,898,814 | 2/1990 | Kwon | 435/6 |
| 5,487,391 | 1/1996 | Boon-Falleur | 435/6 |

OTHER PUBLICATIONS van der Bruggen et al., A gene encoding an antigen recognized by cytolytic T lymphocytes on a human melanoma, Sci. 254: 1643–1647, see Abstracat, p. 1643, col. 1, third sentence, second paragraph, Dec. 1991.

Greenberg, Therapy of murine leukemia with cyclophosphamide and immune lyt–2+ cells: cytolytic T cells can mediate eradication of disseminated leukemia, J. Immunology, Vo. 136, No. 5, p. 1917, col. 2, 1st sentence of the 1st paragraph, Mar. 1986.

Ruppert et al., Multiple transcripts of the mouse tyrosinase gene are generated by alternative splicing, The EMBO J. vol. 7, No. 9, pp. 2715–2722, p. 2715, col. 1, lines 5–7, Jun. 1988.

Traversari, et al., Transfection and expression of a gene coding for a human melanoma antigen recognized by autologous cytolytic T lymphocytes, Immunogenetics 35: 145–152, Abstract, first sentence, p. 146, col. 2, "CTL clones", p. 147, column 1, Sc, 1992.

Brichard, et al, "The Tyrosinase Gene Codes for an Antigen Recognized by Autologous Cytolytic T Lymphocytes on HLA–A2 Melanomas", J. Exp. Med. 178: 489–495 (1993).

Coulie, et al, "Genes Coding For Tumor Antigens Recognized by Human Cytolytic T Lymphocytes", J. Immunotherapy 14: 104–109 (1993).

Slingluff, et al, "Recognition of Human Melanoma Cells by HLA–A2.1 Restricted Cytotoxic T Lymphocytes As Medicated By At Least Six Shared Peptide Epitopes", J. Immunol. 150(7): 2955–2963 (Apr. 1, 1993).

Barinaga, "Getting Some 'Backbone': How MHC Binds Peptides" Science 257: 880–881 (Aug. 14, 1992).

Falk, et al, "Allele Specific Motifs revealed by sequencing of self–peptides eluted from MHC molecules", Nature 351: 290–296 (May 23, 1991).

Wolfel, et al, "Lysis of Human Melanoma Cells by Autologous Cytolytic T Cells Clones", J. Exp. Med. 170: 797–810 (Sep. 1989).

*Primary Examiner*—Ponnathapura Achutamurthy
*Assistant Examiner*—Hankyel T. Park
*Attorney, Agent, or Firm*—Felfe & Lynch

[57] ABSTRACT

The invention relates to the identification of complexes of human leukocyte antigen molecules and tyrosinase derived peptides on the surfaces of abnormal cells. The therapeutic and diagnostic ramifications of this observation are the subject of the invention.

10 Claims, 15 Drawing Sheets

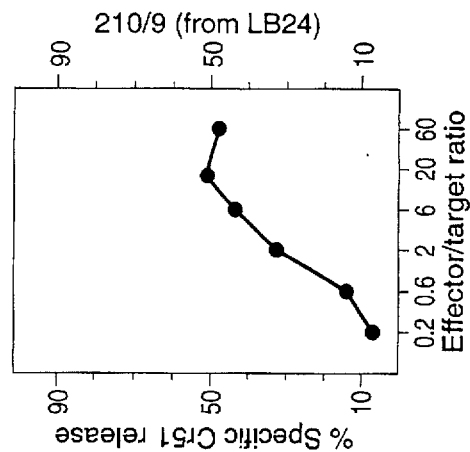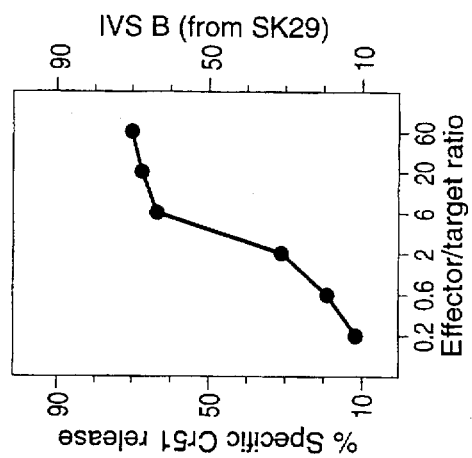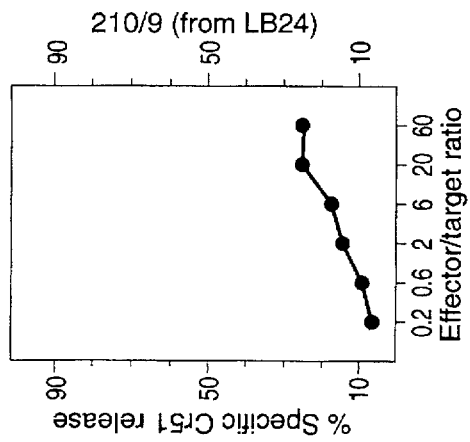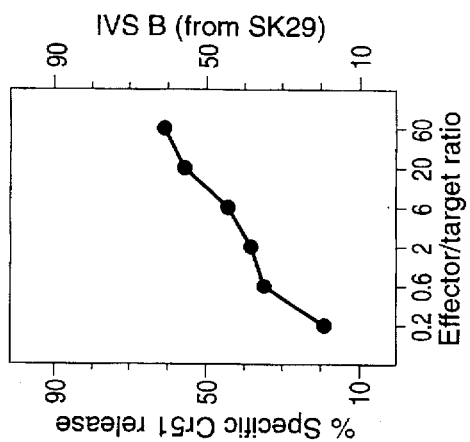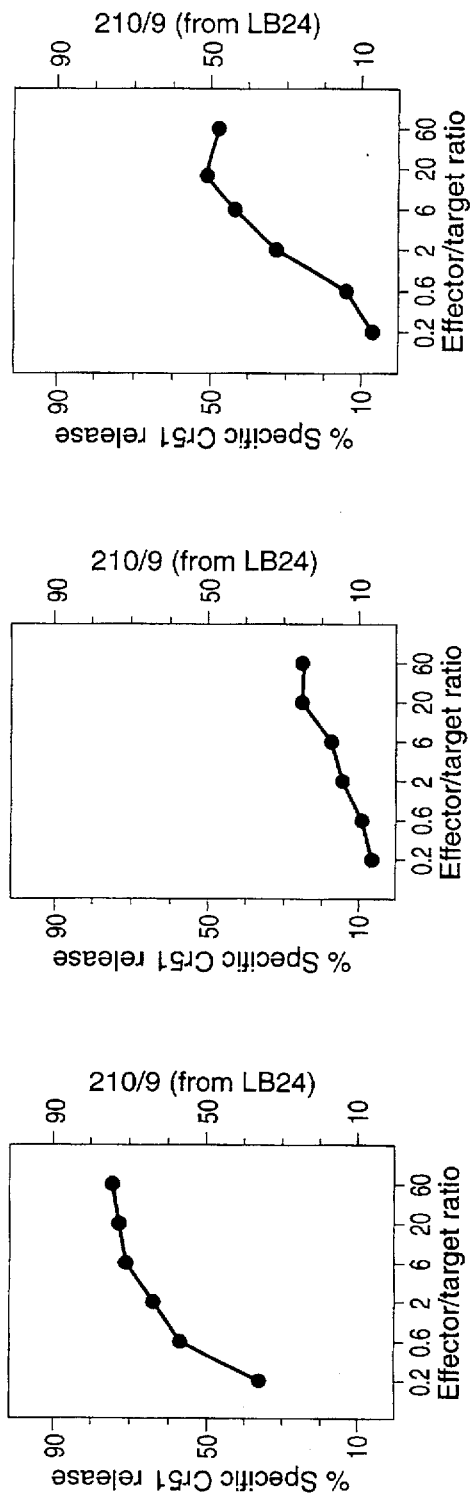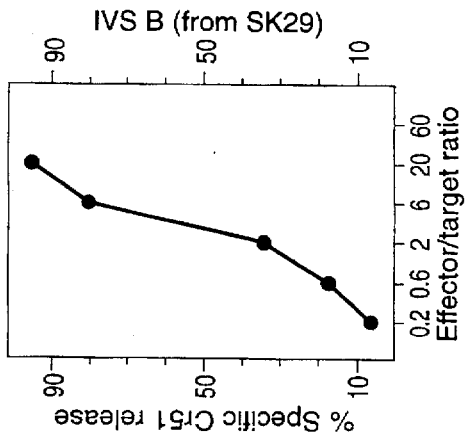

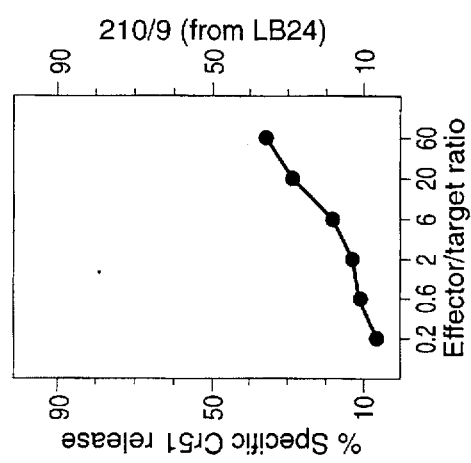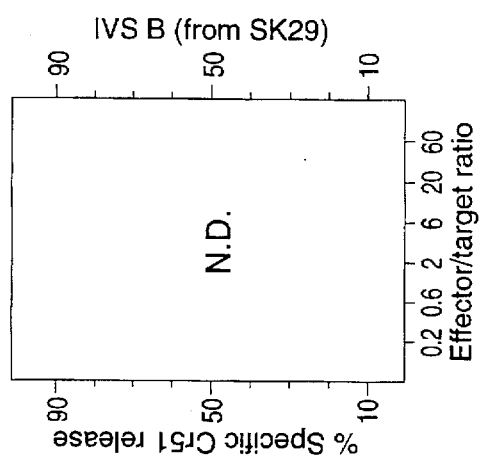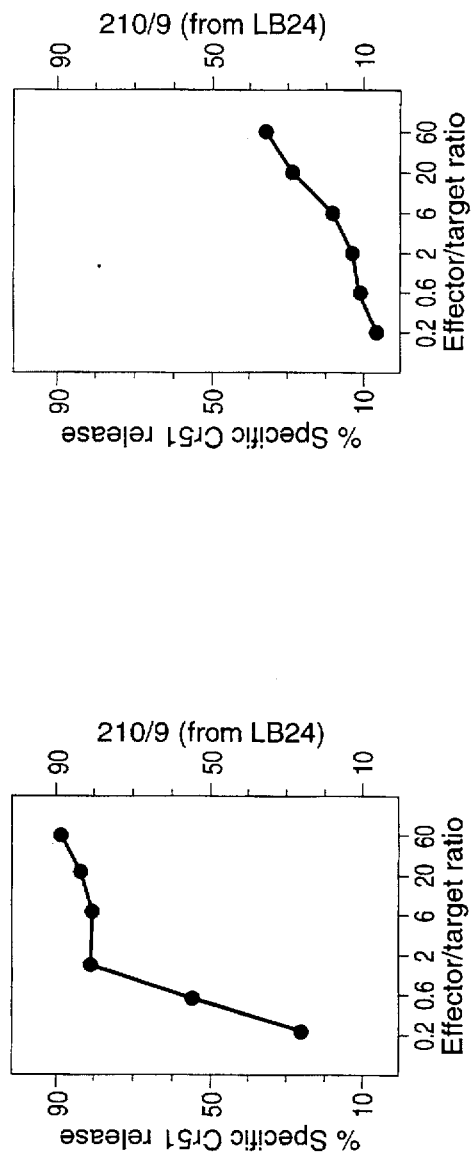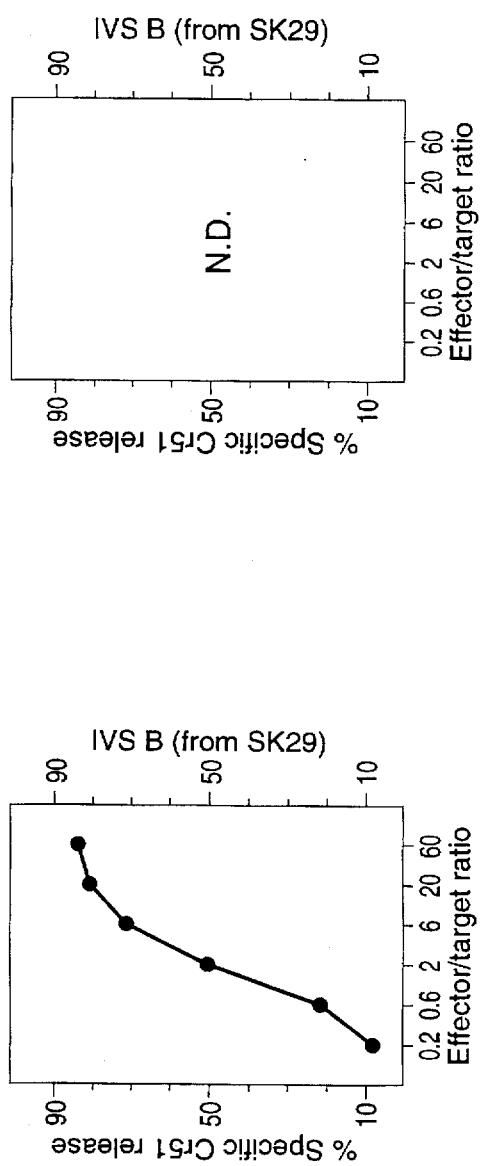

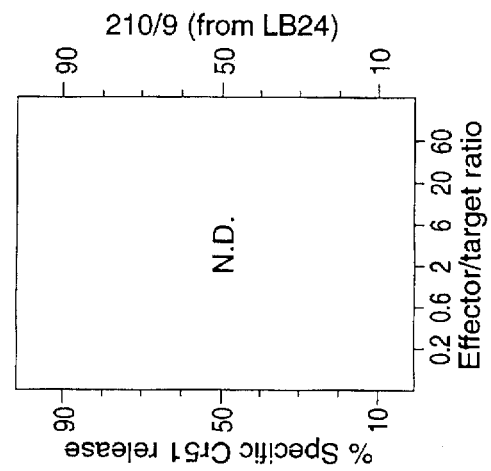
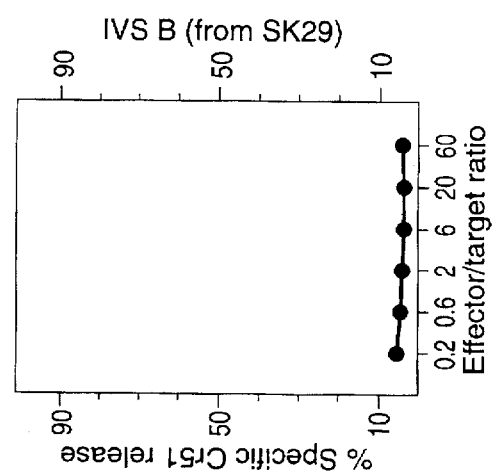
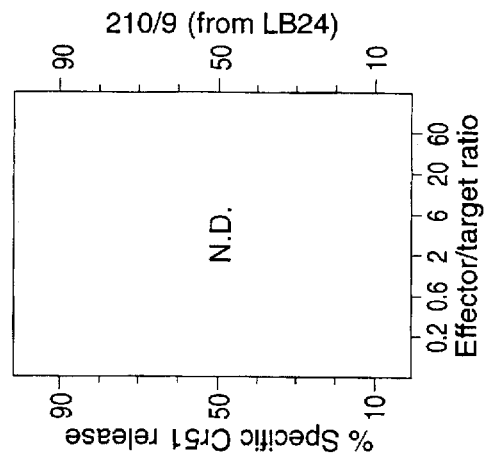
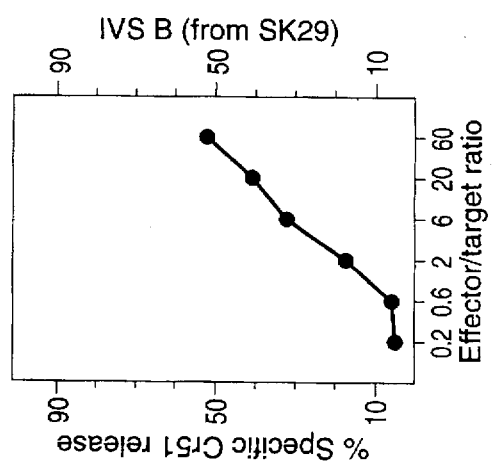
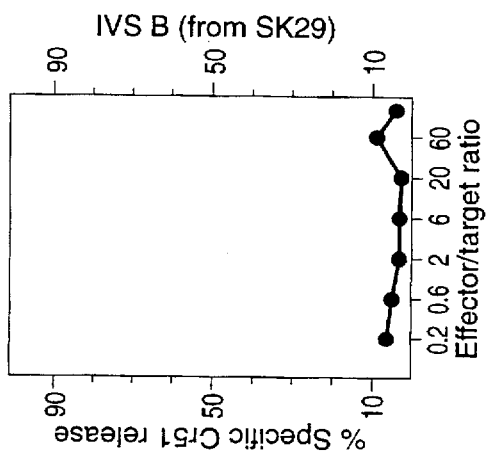

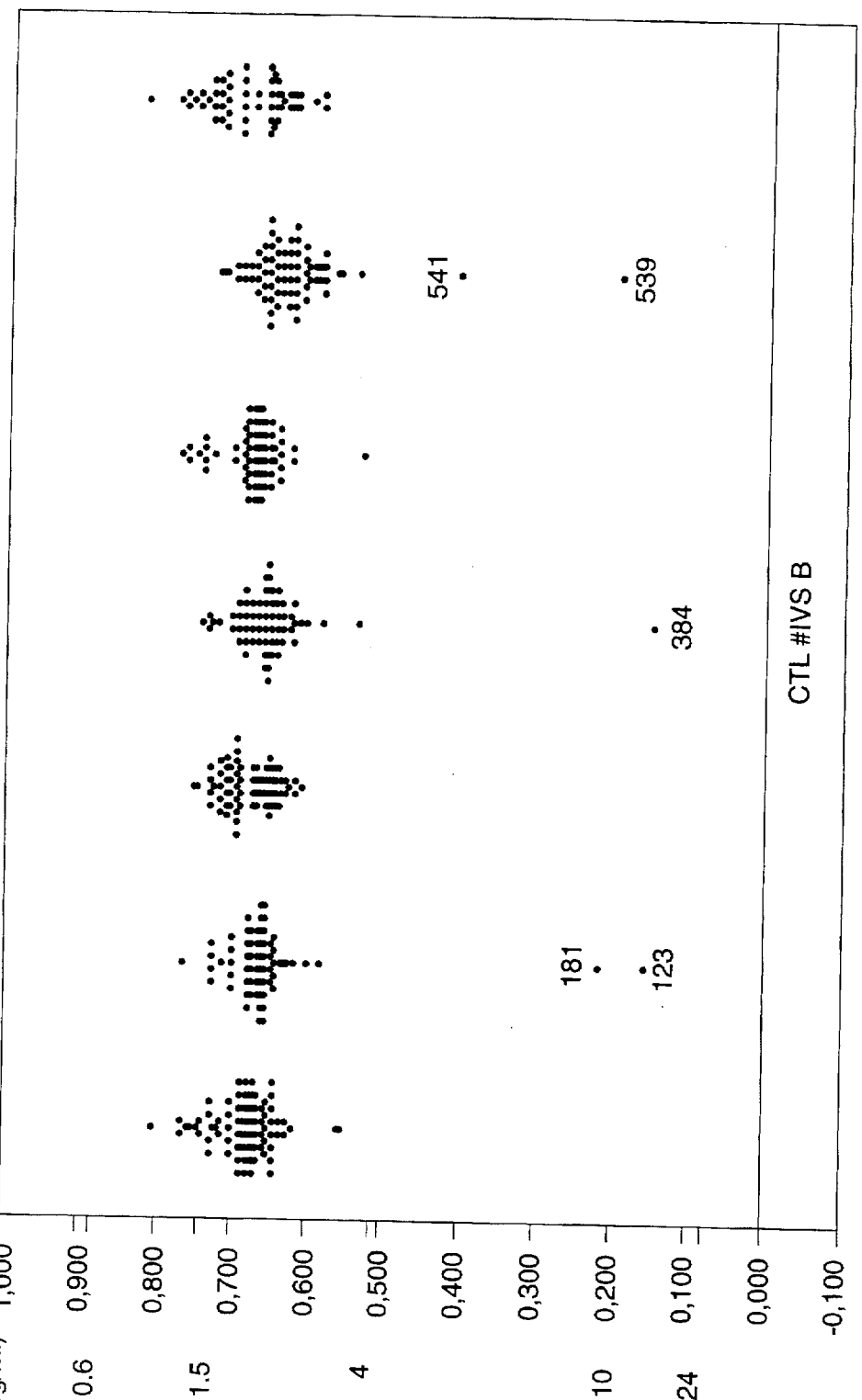

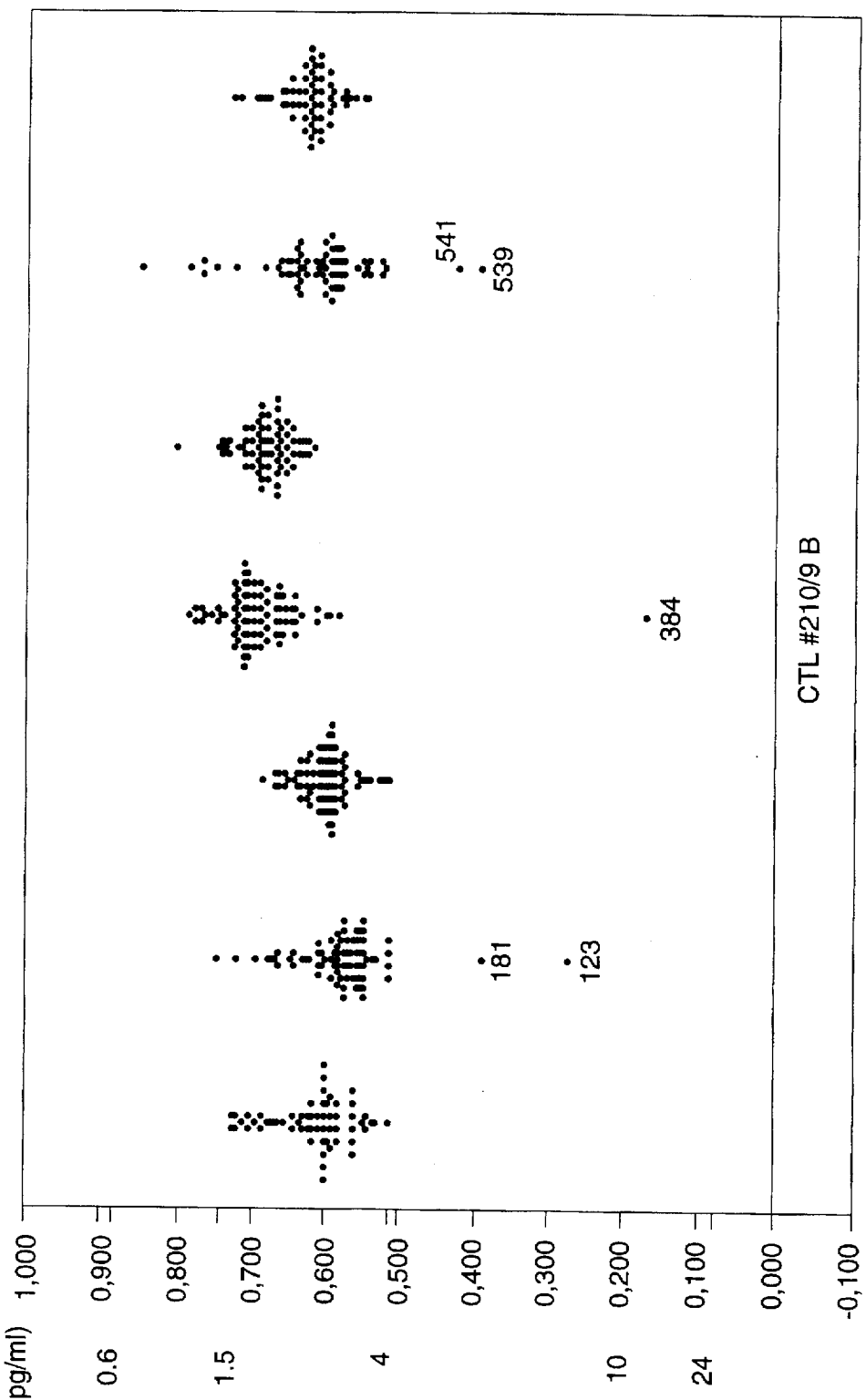

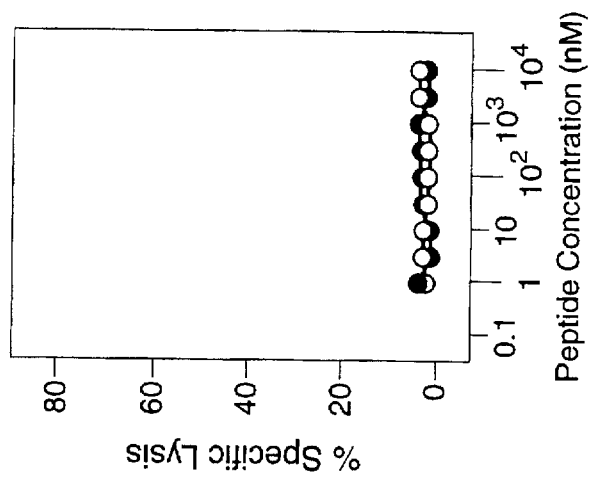
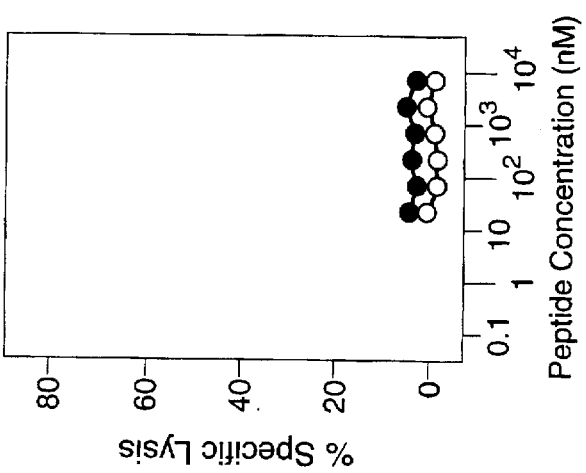
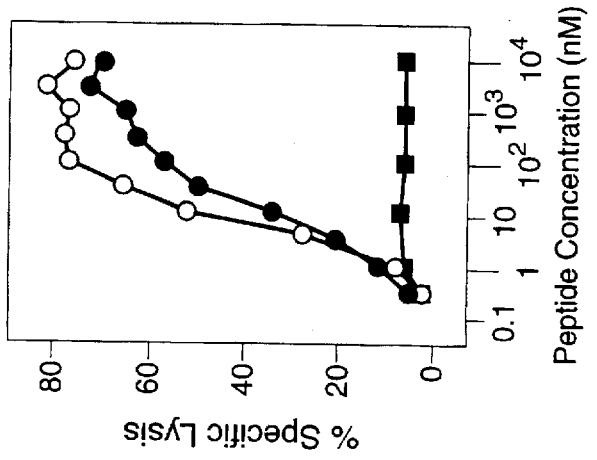

ISOLATED, TYROSINASE DERIVED PEPTIDES AND USES THEREOF

RELATED APPLICATIONS

This application is a continuation-in-part of Ser. No. 08/233,305, filed Apr. 26, 1994, now U.S. Pat. No. 5,519, 117, which is a continuation-in-part of Ser. No. 08/203,054 filed on Feb. 28, 1994, now U.S. Pat. No. 5,530,096, which is a continuation-in-part of application Ser. No. 08/081,673, filed Jun. 23, 1993, now U.S. Pat. No. 5,487,974, which is a continuation in part of copending U.S. patent application Ser. No. 054,714, filed Apr. 28, 1993 which is a continuation-in-part of U.S. patent application Ser. No. 994,928, filed Dec. 22, 1992 now abandoned. All are incorporated by reference.

FIELD OF THE INVENTION

This invention relates to isolated peptides, derived from tyrosinase, which are presented by HLA-A2 and HLA-B44 molecules and uses thereof. In addition, it relates to the ability to identify those individuals diagnosed with conditions characterized by cellular abnormalities whose abnormal cells present complexes of these peptides and HLA-A2 and HLA-B44, the presented peptides, and the ramifications thereof.

BACKGROUND AND PRIOR ART

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLAs"), or major histocompatibility complexes ("MHCs"), and peptides. The peptides are derived from larger molecules which are processed by the cells which also present the HLA/MHC molecule. See in this regard Male et al., *Advanced Immunology* (J. P. Lipincott Company, 1987), especially chapters 6–10. The interaction of T cell and complexes of HLA/peptide is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Recently, much work has focused on the mechanisms by which proteins are processed into the HLA binding peptides. See, in this regard, Barinaga, Science 257: 880 (1992); Fremont et al., Science 257: 919 (1992); Matsumura et al., Science 257: 927 (1992); Latron et al., Science 257: 964 (1992).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes.

In U.S. Pat. Nos. 5,405,940 and 5,462,871, the disclosures of which are incorporated by reference, nonapeptides are taught which bind to the HLA-A1 molecule. The references teach that, given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

The enzyme tyrosinase catalyzes the reaction converting tyrosine to dehydroxyphenylalanine or "DOPA" and appears to be expressed selectively in melanocytes (Muller et al., EMBO J 7: 2715 (1988)). An early report of cDNA for the human enzyme is found in Kwon, U.S. Pat. No. 4,898,814. A later report by Bouchard et al., J. Exp. Med. 169: 2029 (1989) presents a slightly different sequence. A great deal of effort has gone into identifying inhibitors for this enzyme, as it has been implicated in pigmentation diseases. Some examples of this literature include Jinbow, WO9116302; Mishima et al., U.S. Pat. No. 5,077,059, and Nazzaropor, U.S. Pat. No. 4,818,768. The artisan will be familiar with other references which teach similar materials.

U.S. patent application Ser. No. 08/081,673, filed Jun. 23, 1993 and incorporated by reference, teaches that tyrosinase may be treated in a manner similar to a foreign antigen or a TRAP molecule—i.e., it was found that in certain cellular abnormalities, such as melanoma, tyrosinase is processed and a peptide derived therefrom forms a complex with HLA molecules on certain abnormal cells. These complexes were found to be recognized by cytolytic T cells ("CTLs"), which then lyse the presenting cells. The ramifications of this surprising and unexpected phenomenon were discussed. Additional peptides have now been found which also act as tumor rejection antigens presented by HLA-A2 molecules. These are described in Ser. No. 08/203,054, filed Feb. 28, 1994 and incorporated by reference.

It has now been found that additional peptides derived from tyrosinase are tumor rejection antigens in that they are presented by MHC molecule HLA-B44, and are lysed by cytolytic T cells.

BRIEF DESCRIPTION OF THE FIGURES

FIG. 1 describes, collectively, cell lysis studies. In particular:

FIG. 1A shows lysis of cell line LB24-MEL;

FIG. 1B shows lysis of cell line SK29-MEL;

FIG. 1C shows lysis of cell line LB4.MEL;

FIG. 1D shows lysis of cell line SK23.MEL;

FIG. 1E shows lysis of cell line LE516.MEL;

FIG. 1G shows lack of lysis of MZ2-MEL;

FIG. 1H shows lysis studies on NK target K562;

FIG. 1I shows lysis of the loss variant in FIG. 1F after transfection with a gene for HLA-A2.

FIG. 2 presents studies of TNF release of CTL IVSB.

FIG. 3 depicts studies of TNF release of CTL 210/9.

In FIG. 7, the symbol "○" is used for cell line T2, "■" for MZ2-MEL not presenting HLA-A2, and "●" for MZ2-MEL which has been transfected to present HLA-A2. Example 12 elaborates on these tests.

In FIG. 8A, the cell line ("Rosi EBV") was preincubated with monoclonal antibody W6/32, whereas in FIG. 8B, there was no preincubation.

DETAILED DESCRIPTION OF PREFERRED EMBODIMENTS

Example 1

Melanoma cell lines SK 29-MEL (also referred to in the literature as SK MEL-29) and LB24-MEL, which have been available to researchers for many years, were used in the following experiments.

Samples containing mononuclear blood cells were taken from patients SK29 (AV) and LB24 (these patients were also the source of SK 29-MEL and LB24-MEL, respectively). The melanoma cell lines were contacted to the mononuclear blood cell containing samples. The mixtures were observed for lysis of the melanoma cell lines, this lysis indicating that cytolytic T cells ("CTLs") specific for a complex of peptide and HLA molecule presented by the melanoma cells were present in the sample.

The lysis assay employed was a chromium release assay following Herin et al., Int. J. Cancer 39:390–396 (1987), the disclosure of which is incorporated by reference. The assay, however, is described herein. The target melanoma cells were grown in vitro, and then resuspended at $10^7$ cells/ml in DMEM, supplemented with 10 mM HEPES and 30% FCS, and incubated for 45 minutes at 37° C. with 200 μCi/ml of Na($^{51}$Cr)O$_4$. Labelled cells were washed three times with DMEM, supplemented with 10 mM Hepes. These were then resuspended in DMEM supplemented with 10 mM Hepes and 10% FCS, after which 100 ul aliquots containing $10^3$ cells, were distributed into 96 well microplates. Samples of PBLs were added in 100 ul of the same medium, and assays were carried out in duplicate. Plates were centrifuged for 4 minutes at 100 g, and incubated for four hours at 37° C. in a 5.5% of CO$_2$ atmosphere.

Plates were centrifuged again, and 100 ul aliquots of supernatant were collected and counted. Percentage of $^{51}$Cr release was calculated as follows:

$$\% \,^{51}Cr\ release = \frac{(ER - SR)}{(MR - SR)} \times 100$$

where ER is observed, experimental $^{51}$Cr release, SR is spontaneous release measured by incubating $10^3$ labeled cells in 200 ul of medium alone, and MR is maximum release, obtained by adding 100 ul 0.3% Triton X-100 to target cells.

Those mononuclear blood samples which showed high CTL activity were expanded and cloned via limiting dilution, and were screened again, using the same methodology.

The same method was used to test target K562 cells. When EBV-transformed B cells (EBV-B cells) were used, the only change was the replacement of DMEM medium by Hank's medium, supplemented with 5% FCS.

These experiments led to isolation of CTL clone "IVSB" from patient SK29 (AV) and CTL clone 210/9 from patient LB24.

Figure 1F:
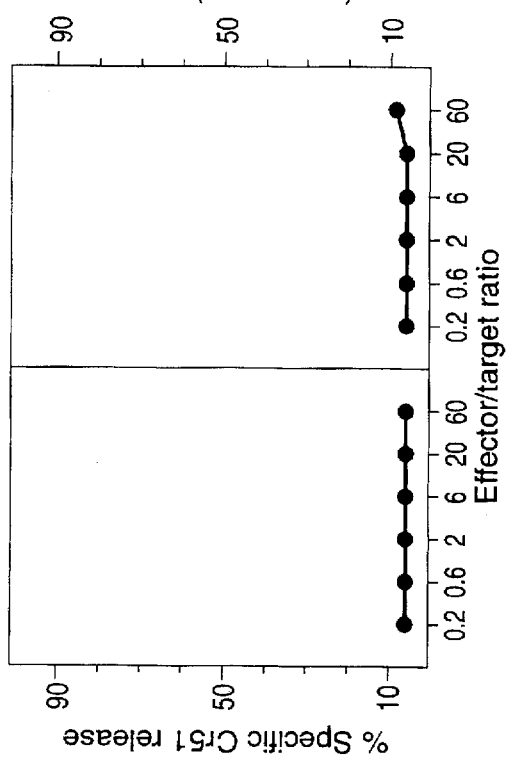
FIG. 1F shows lysis of cell line SK29-MEL.1.22 which has lost HLA-A2 expression.
Figure 1F:
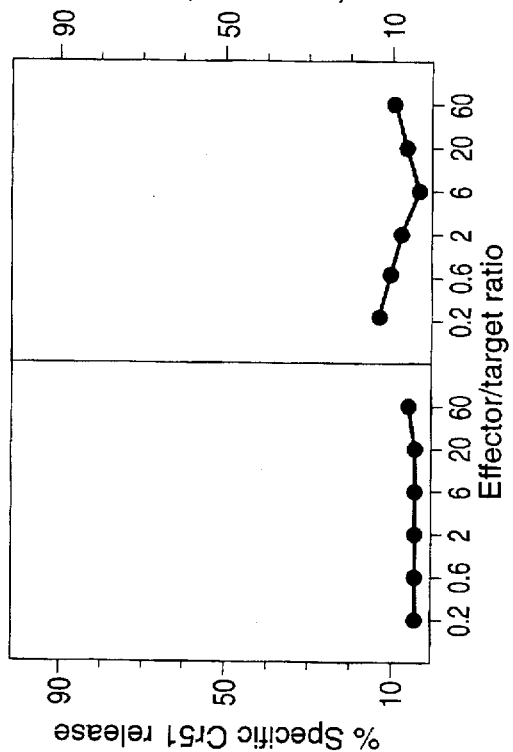

FIG. 1 presents the results of these assays, in panels A, B, G and I. Specifically, it will be seen that both CTLs lysed both melanoma cell lines, and that there was no lysis of the K562 and EBV-B cell lines.

Example 2

The CTLs described were tested against other melanoma cell lines to determine whether their target was shared by other melanoma cell lines. Lysis as described in Example 1 was studied for lines LB4.MEL, SK23.MEL (also known as SK MEL-23), and LE516.MEL. FIG. 1, panels C, D and E shows that the clones did lyse these lines.

The tested lines are known to be of type HLA-A2, and the results suggested that the CTLs are specific for a complex of peptide and HLA-A2. This suggestion was verified by testing a variant of SK 29-MEL which has lost HLA-A2 expression. FIG. 1, panel F shows these results. Neither clone lysed the HLA-loss variant. When the variant was transfected with the HLA-A2 gene of SK29-MEL, however, and retested, lysis was observed. Thus, it can be concluded that the presenting molecule is HLA-A2.

Example 3

Once the presenting HLA molecule was identified, studies were carried out to identify the molecule, referred to hereafter as the "tumor rejection antigen precursor" or "TRAP" molecule which was the source of the presented peptide.

To do this, total RNA was isolated from cell line SK29-MEL.1, which is a subclone of SK29-MEL. The RNA was isolated using an oligo-dT binding kit, following well recognized techniques. Once the total RNA was secured, it was transcribed into cDNA, again using standard methodologies. The cDNA was then ligated to EcoRI adaptors and cloned into the EcoRI site of plasmid pcDNA-I/Amp, in accordance with manufacturer's instructions. The recombinant plasmids were then electroporated into JM101 E. coli (electroporation conditions: 1 pulse at 25 μfarads, 2500 V).

The transfected bacteria were selected with ampicillin (50 μg/ml), and then divided into 700 pools of 200 clones each. Each pool represented about 100 different cDNAs, as analysis showed that about 50% of plasmids contained an insert. Each pool was amplified to saturation, and plasmid DNA was isolated via alkaline lysis, potassium acetate precipitation and phenol extraction, following Maniatis et al., in Molecular Cloning: A Laboratory Manual (Cold Spring Harbor, N.Y., 1982). Cesium gradient centrifugation was not used.

Example 4

The amplified plasmids were then transfected into eukaryotic cells. Samples of COS-7 cells were seeded, at 15,000 cells/well into tissue culture flat bottom microwells, in Dulbecco's modified Eagles Medium ("DMEM") supplemented with 10% fetal calf serum. The cells were incubated overnight at 37° C., medium was removed and then replaced by 30 µl/well of DMEM medium containing 10% Nu serum, 400 µg/ml DEAE-dextran, 100 µM chloroquine, 100 ng of plasmid pcDNA-I/Amp-A2 and 100 ng of DNA of a pool of the cDNA library described supra. Plasmid pcDNA-I/Amp-A2 contains the HLA-A2 gene from SK29-MEL. Following four hours of incubation at 37° C., the medium was removed, and replaced by 50 µl of PBS containing 10% DMSO. This medium was removed after two minutes and replaced by 200 µl of DMEM supplemented with 10% of FCS.

Following this change in medium, COS cells were incubated for 48 hours at 37° C. Medium was then discarded, and 2000 cells of either of the described CTL clones were added, in 100 µl of Iscove's medium containing 10% pooled human serum. When clone 210/9 was used, the medium was supplemented with 25 U/ml of IL-2. Supernatant was removed after 24 hours, and TNF content was determined in an assay on WEHI cells, as described by Traversari et al., Immunogenetics 35: 145–152 (1992), the disclosure of which is incorporated by reference.

Of 700 wells tested with IVSB, 696 showed between 0.6 and 4 pg of TNF per ml. The remaining four wells contained between 10 and 20 pg/ml of TNF. Homologous wells tested with CTL 210/9 showed similar, clearly higher values. FIGS. 2 and 3 present these data.

Example 5

Three of the four pools identified as high producers (numbers "123", "181" and "384") were selected for further experiments. Specifically, the bacteria were cloned, and 570 bacteria were tested from each pool. Plasmid DNA was extracted therefrom, transfected into a new sample of COS cells in the same manner as described supra, and the cells were again tested for stimulation of CTL 210/9 and CTL IVSB. A positive clone was found in pool 123 ("p123.B2"), and one was found in pool 384 ("p384.C6"). Convincing evidence that the transfected cells were recognized by CTLs was obtained by carrying out a comparative test of COS cells transfected with cDNA and the HLA-A2 gene, and COS cells transfected only with HLA-A2. TNF release in CTL supernatant was measured by testing it on WEHI cells. The optical density of the surviving WEHI cells was measured using MTT. Results are presented in Table 1:

TABLE 1

|  | cDNA (123.B2) + HLA-A2 DNA | no cDNA + HLA-A2 |
| --- | --- | --- |
| Run 1 | 0.087 | 0.502 |
| Run 2 | 0.108 | 0.562 |

The values for WEHI OD's correspond to 24 pg/ml of TNF for cDNA and HLA-A2, versus 2.3 pg/ml for the control.

The plasmids from the positive clones were removed, and sequenced following art known techniques. A sequence search revealed that the plasmid insert was nearly identical to the cDNA for human tyrosinase, as described by Bouchard et al., J. Exp. Med. 169: 2029 (1989), the disclosure of which is incorporated by reference. Thus, a normally occurring molecule (i.e., tyrosinase), may act as a tumor rejection antigen precursor and be processed to form a peptide tumor rejection antigen which is presented on the surface of a cell, in combination with HLA-A2, thereby stimulating lysis by CTL clones. The nucleic sequence of the identified molecule is presented as SEQ ID NO: 1.

Example 6

Prior work reported by Chomez et al., Immunogenetics 35: 241 (1992) has shown that small gene fragments which contain a sequence coding for an antigenic peptide resulted in expression of that peptide. This work, which is incorporated by reference in its entirety, suggested the cloning of small portions of the human tyrosinase cDNA described supra and in SEQ ID NO: 1. Using the methodologies described in examples 1–5, various fragments of the cDNA were cotransfected with a gene for HLA-A2 in COS-7 cells, and TNF release assays were performed. These experiments led to identification of an approximately 400 base pair fragment which, when used in cotransfection experiments, provoked TNF release from cytolytic T cell clone CTL IVSB discussed supra, shown to be specific for HLA-A2 presenting cells. The approximately 400 base pair fragment used corresponded to bases 711 to 1152 of SEQ ID NO: 1. The amino acid sequence for which the fragment codes was deduced, and this sequence was then compared to the information provided by Hunt et al., Science 255: 1261 (1992), and Falk et al., Nature 351: 290 (1991), the disclosures of which are both incorporated by reference in their entirety. These references discuss consensus sequences for HLA-A2 presented peptides. Specifically, Hunt discusses nonapeptides, where either Leu or Ile is always found at the second position, Leu being the "dominant residue". The ninth residue is described as always being a residue with an aliphatic hydrocarbon side chain. Val is the dominant residue at this position. Hunt discusses a strong signal for Leu and an intermediate signal for Met at the second position, one of Val, Leu, Ile or Thr at position 6, and Val or Leu at position 9, with Val being particularly strong. On the basis of the comparison, nonapeptides were synthesized and then tested to see if they could sensitize HLA-A2 presenting cells. To do so, tyrosinase loss variant cell lines SK29-MEL 1.218 and T202LB were used. Varying concentrations of the tested peptides were added to the cell lines, together with either of cytolytic T cell clone CTL IVSB or cytolytic T cell clone CTL 210/9. Prior work, described supra, had established that the former clone lysed tyrosinase expressing cells which present HLA-A2, and that the latter did not.

The tyrosinase loss variants were incubated for one hour in a solution containing $^{51}Cr$, at 37° C., either with or without anti HLA-A2 antibody MA2.1, which was used to stabilize empty HLA-A2 molecules. In the tests, cells were washed four times, and then incubated with varying dilutions of the peptides, from 100 µM down to 0.01 µM. After 30 minutes, effector cells were added at an E/T ratio of 40/1 and four hours later, 100 µl of supernatant were collected and radioactivity counted.

Figure 4A:
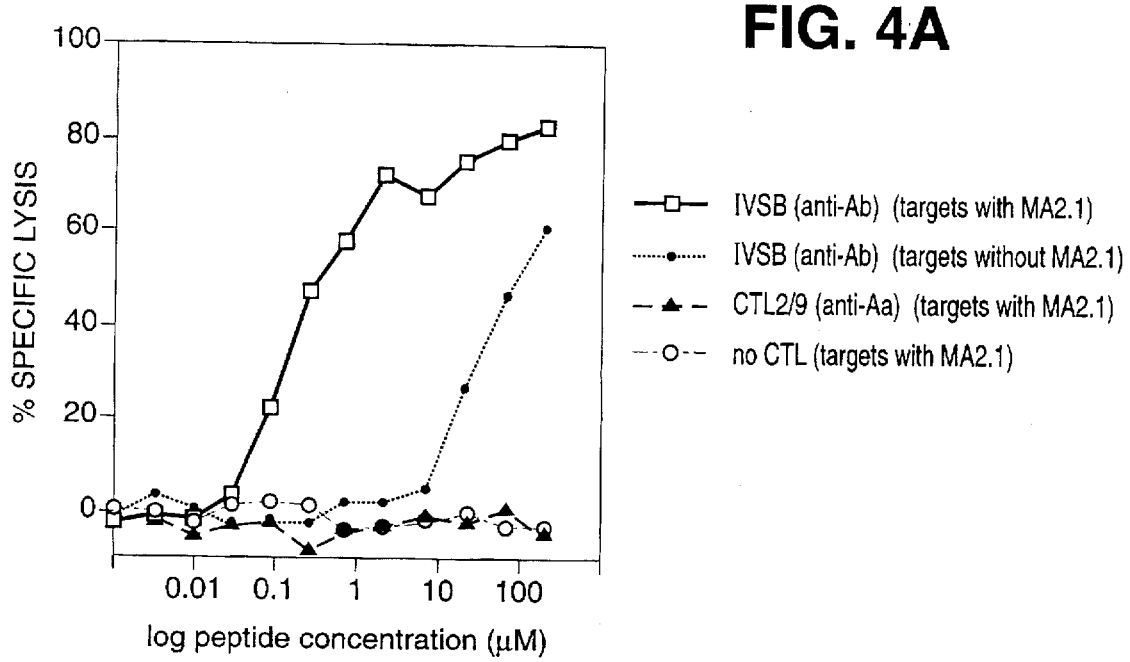
FIG. 4 depicts the recognition of the peptide of SEQ ID NO: 2 by cytolytic T cell clone CTL-IVSB but not cytolytic T cell clone CTL 2/9.
Figure 4B:
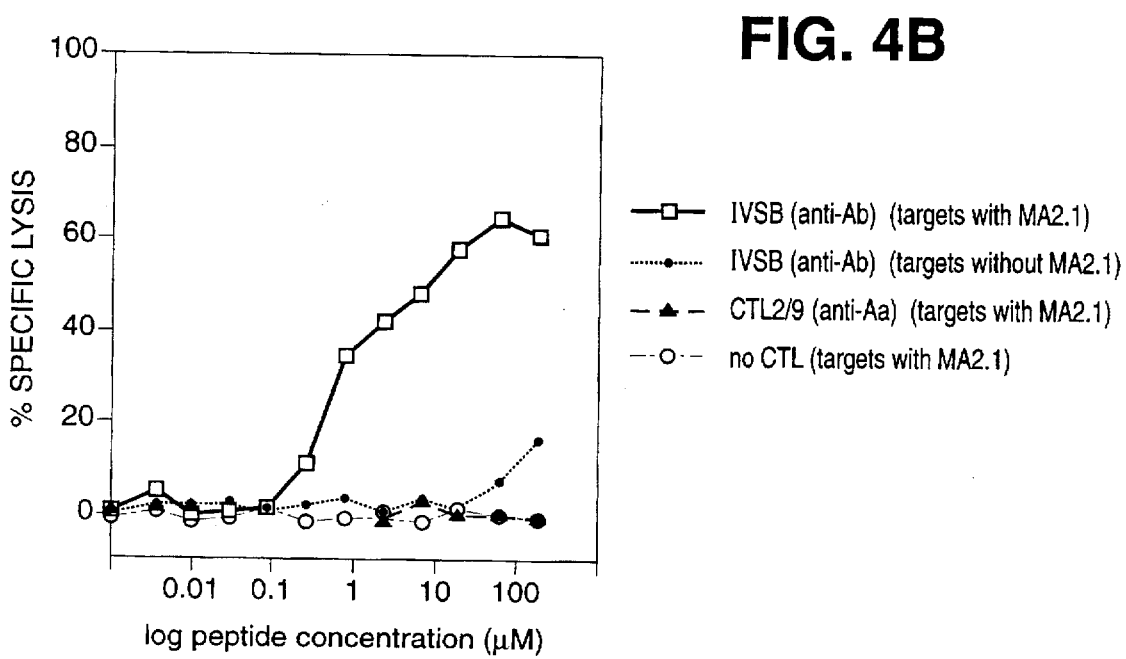
Figure 5:
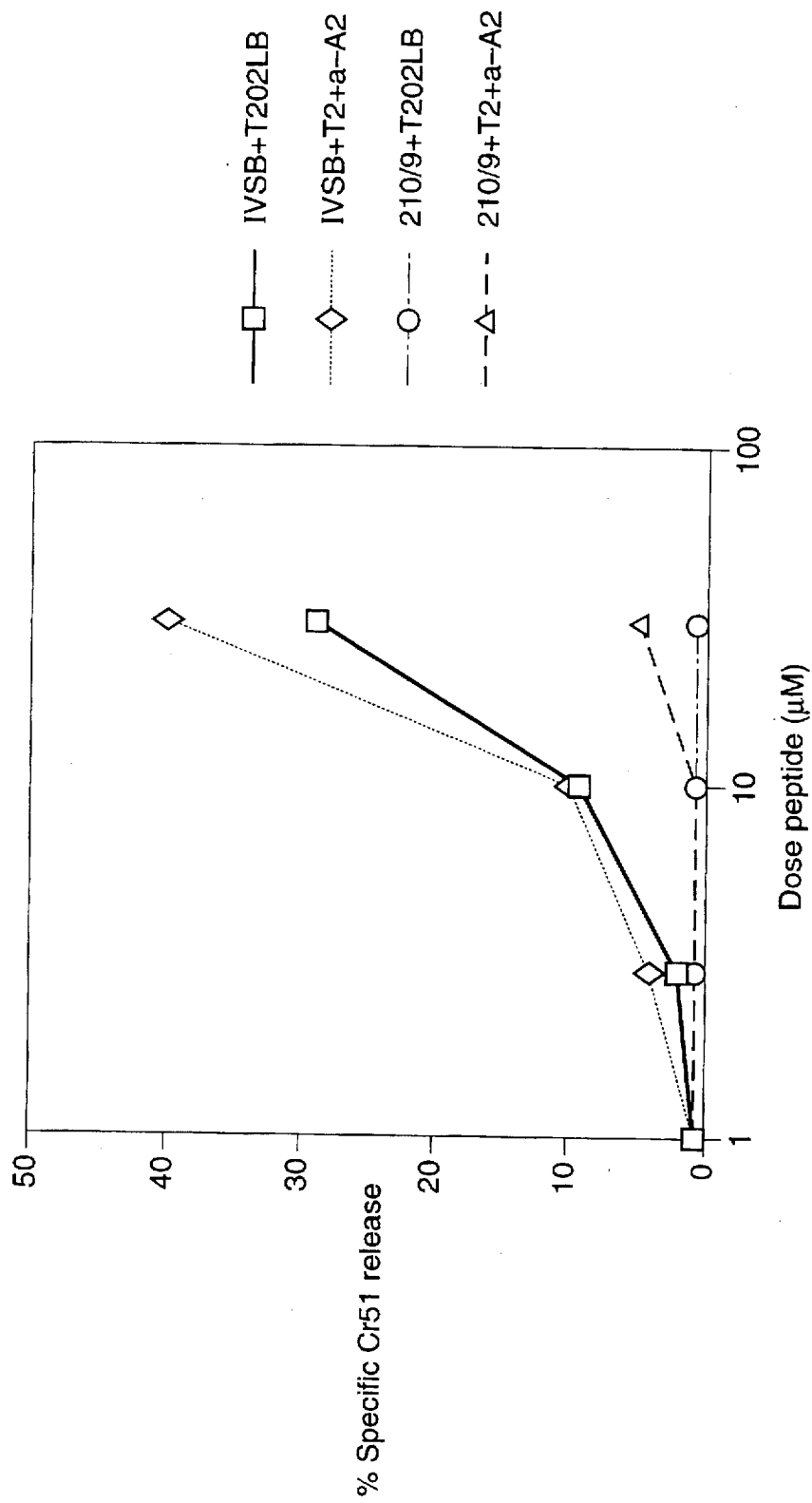
FIG. 5 shows that the peptide of SEQ ID NO: 2 is not recognized by cytolytic T cell clone CTL 210/9.

FIG. 4 shows the results obtained with nonapeptide

Tyr Met Asn Gly Thr Met Ser Gln Val. (SEQ ID NO: 2)

This peptide, referred to hereafter as SEQ ID NO: 2, corresponds to residues 1129–1155 of the cDNA sequence for tyrosinase presented in SEQ ID NO: 1. Complexes of HLA-A2 and this peptide are recognized by CTL clone IVSB.

In a parallel experiment, it was shown that CTL clone CTL 210/9, derived from patient LB24, did not recognize the complexes of HLA-A2 and the peptide of SEQ ID NO: 2, although it did recognize complexes of HLA-A2 and a tyrosinase derived peptide. Thus, tyrosinase is processed to at least one additional peptide which, when presented by HLA-A2 molecules, is recognized by CTL clones.

Example 7

In a follow-up experiment, a second gene fragment which did not encode the peptide of SEQ ID NO: 2 was used. This fragment began at base 1 and ended at base 1101 of SEQ ID NO: 1 (i.e. the EcoRI-SphI fragment). Cytolytic T cell clone CTL 210/9, discussed supra, was tested against COS-7 cells transfected with this fragment in the manner described supra. CTL IVSB was also tested. These results showed that CTL 210/9 recognized an antigen on the surface of HLA-A2 expressing cells transfected with this fragment, but CTL IVSB did not. Thus, a second tumor rejection antigen peptide is derived from tyrosinase.

Example 8

In order to further define the tumor rejection antigen recognized by CTL 210/9, the following experiments were carried out.

A second fragment, corresponding to bases 451–1158 of SEQ ID NO: 1 was transfected into COS cells together with a gene for HLA-A2, and TNF release assays were carried out. This sequence provoked TNF release from clone CTL IVSB (20 pg/ml), but not from CTL 210/9 (3.8 pg/ml). These results confirmed that the two CTL clones recognize different peptides, and that the peptide recognized by LB24-CTL 210/9 must be encoded by region 1–451.

Example 9

The tyrosinase derived peptide coded for by cDNA fragment 1–451 was analyzed for consensus sequences known to bind HLA-A2. The peptides corresponding to these consensus sequences were synthesized, and tested for their ability to sensitize HLA-A2 presenting cells. To do so, two tyrosinase negative melanoma cell lines were used (i.e., NA8-MEL, and MZ2-MEL 2.2 transfected with HLA-A2), and cell line T2, as described by Salter et al, Immunogenetics 21: 235–246 (1985)).

The cells were incubated with $^{51}$Cr, and monoclonal antibody MA2.1, which is specific for HLA-A2, for 50 minutes at 370° C., followed by washing (see Bodmer et al., Nature 342: 443–446 (1989), the disclosure of which is incorporated by reference in its entirety). Target cells were incubated with various concentrations of the peptides, and with either of LB 24-CTL clones 210/5 or 210/9. The percent of chromium release was measured after four hours of incubation.

The peptide Met Leu Leu Ala Val Leu Tyr Cys Leu Leu (SEQ ID NO: 3) was found to be active.

In further experiments summarized here, CTL-IVSB previously shown to recognize SEQ ID NO: 2, did not recognize the peptide of SEQ ID NO: 3.

The results are summarized in Tables 2–4 which follow:

TABLE 2

| | PEPTIDE | |
|---|---|---|
| | SEQ ID NO: 2 | SEQ ID NO: 3 |
| CTL-IVSB | + | + |
| CTL-210/5 | – | + |
| CTL-210/9 | – | + |

TABLE 3

3j93-Lysis of MZ2-2.2-A2 sensitized with tyrosinase peptides by LB24-CTL 210/5 and 210/9, and SK29-CTL IVSB

| Effectors | Peptides | Dose | MZ2.2.2.A2 + anti-A2* |
|---|---|---|---|
| LB24-CTL 210/5 (44:1) | MLLAVLYCLL (LAUS 17-5) | 10 μM | 18 |
| | | 3 | 17 |
| | | 1 | 16 |
| | YMNGTMSQV (MAINZ) | 30M | 1 |
| | | 10 | 1 |
| | | 3 | 1 |
| LB24-CTL 210/9 (30:1) | MLLAVLYCLL (LAUS 17-5) | 10 μM | 18 |
| | | 3 | 17 |
| | | 1 | 15 |
| | YMNGTMSQV (MAINZ) | 30M | 1 |
| | | 10 | 1 |
| | | 3 | 1 |
| SK29-CTL IVSB (40:1) | MLLAVLYCLL (LAUS 17-5) | 10 μM | 1 |
| | | 3 | 1 |
| | | 1 | 1 |
| | YMNGTMSQV (MAINZ) | 30 μM | 68 |
| | | 10 | 68 |
| | | 3 | 62 |

*Target cells were incubated with Cr51 and mono-Ab MA2.1 (anti-HLA-A2) for 50 min, then washed 3 times. They were incubated with various concentrations of peptides for 30 min.
CTL cells were added at the indicated (E:T) ratio. The % specific Cr51 release was mesured after 4h incubation

TABLE 4

Test of tyrosinase peptides recognized by LB24-CTL 210/5 and 210/9 or SK29-CTL IVSB
(% Cr51 specific release)

| Effectors | Peptides | Dose | NAB-MEL* | MZ2-2.2: A2 | T2 |
|---|---|---|---|---|---|
| LB24-CTL 210/5 (41:1) | MLLAVLYCLL (LAUS 17-5) | 10 μM | 30 | 31 | 36 |
| | | 3 | 23 | 27 | 35 |
| | | 1 | 17 | 20 | 26 |
| | | 300 nM | 6 | 17 | 16 |
| | | 100 | 2 | 8 | 5 |
| | | 30 | 3 | 5 | 2 |
| | | 0 | 0 | 0 | 0 |
| LB24-CTL 210/9 (26:1) | MLLAVLYCLL (LAUS 17-5) | 10 μM | 14 | 19 | 21 |
| | | 3 | 13 | 17 | 20 |
| | | 1 | 9 | 14 | 13 |
| | | 300 nM | 3 | 9 | 5 |
| | | 100 | 1 | 1 | 1 |
| | | 30 | 0 | 1 | 0 |
| | | 0 | 0 | 1 | 0 |
| SK29-CTL IVSB (42:1) | YMNGTMSQV (MAINZ) | 10 μM | 46 | 46 | 59 |
| | | 3 | 38 | 44 | 52 |
| | | 1 | 27 | 40 | 46 |
| | | 300 nM | 14 | 22 | 34 |
| | | 100 | 3 | 13 | 21 |
| | | 30 | 1 | 9 | 10 |
| | | 10 | 1 | 3 | 3 |
| | | 3 | 0 | 3 | 4 |
| | | 1 | 0 | 1 | 0 |
| | | 0 | 0 | 4 | 0 |

TABLE 4-continued

Test of tyrosinase peptides recognized by LB24-CTL 210/5 and 210/9 or SK29-CTL IVSB
(% Cr51 specific release)

| Effectors | Peptides | Dose | NAB-MEL* | MZ2-2.2:A2 | T2 |
|---|---|---|---|---|---|
| spt. rel. | | | 339 | 259 | 198 |
| max-spt | | | 2694 | 1693 | 1206 |
| % | | | 11 | 13 | 14 |

Example 10

Additional experiments were carried out using CTL clone 22/31. This clone had previously been shown to lyse subline MZ2-MEL.43 from autologous melanoma cell line MZ2-MEL, but did not lyse other sublines, such as MZ2-MEL 3.0 and MZ2-MEL 61.2, nor did it lyse autologous EBV transformed B cells, or killer cell line K562 (see Van den Eynde et al., Int. J. Cancer 44: 634–640 (1989)). The antigen presented by MZ2-MEL.43 is referred to as antigen C.

In prior work including that reported in the parent of this application, it was found that the tyrosinase gene encodes an antigen recognized by autologous CTLs on most HLA-A2 expressing melanomas. Expression of this gene in sublines of cell line MZ2-MEL was tested by PCR amplification. Clone MZ2-MEL.43 was found to be positive, whereas other MZ2-MEL clones, such as MZ2-MEL.3.0 were negative. Correlation of expression of the tyrosinase gene, and antigen MZ2-C, suggested that MZ2-C might be a tumor rejection antigen derived from tyrosinase, and presented by an HLA molecule expressed by MZ2-MEL. This cell line does not express HLA-A2, which would indicate that if a tyrosinase derived peptide were presented as a TRA, a second HLA molecule was implicated.

Figure 6:
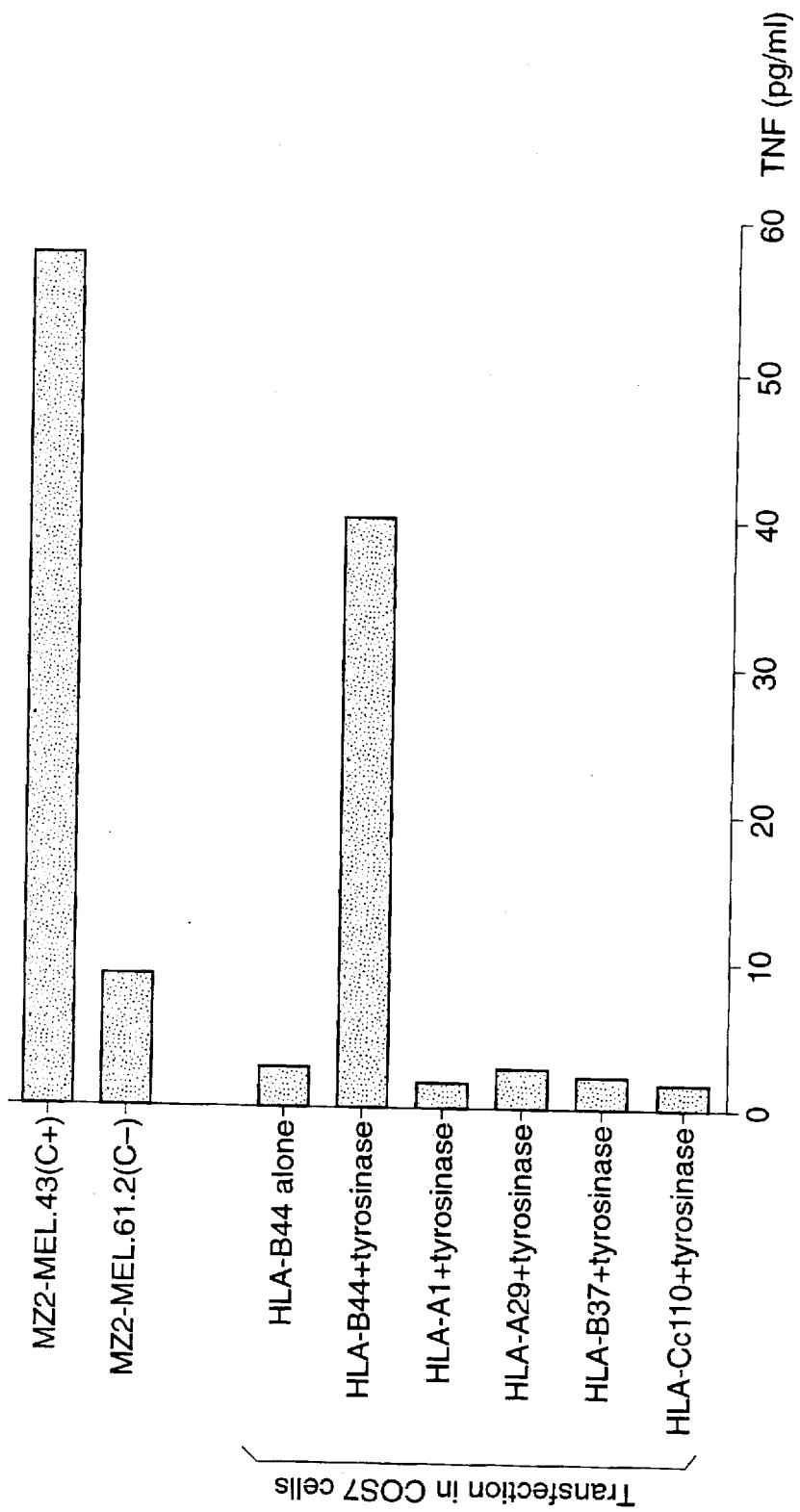
FIG. 6 shows the results obtained when TNF release assays were carried out on various cells, including those which present HLA-B44 on their surface.

Studies were carried out to identify which HLA molecule presented antigen C to CTL 22/31. To determine this, cDNA clones of the HLA molecules known to be on the cell surface, i.e., HLA-A29, HLA-B37, HLA-B 44.02, and HLA-C clone 10, were isolated from an MZ2-MEL.43 cDNA library, and then cloned into expression vector pcDNAI/Amp. Recipient COS 7 cells were then transfected with one of these constructs or a construct containing HLA-A1, plus cDNA coding for tyrosinase (SEQ ID NO: 1). The contransfection followed the method set forth above. One day later CTL 22/31 was added, and 24 hours later, TNF release was measured by testing cytotoxicity on WEHI-164-13, following Traversari et al, supra. FIG. 6 shows that TNF was released by CTL 22/31 only in the presence of cells transfected with both HLA-B44 and tyrosinase. The conclusion to be drawn from this is that HLA-B44 presents a tyrosinase derived tumor rejection antigen.

Example 11

The experiments described supra showed, inter alia, that the decamer of SEQ ID NO: 3 effectively induced lysis of HLA-A2 presenting cells. It is fairly well accepted that MHC molecules present nonapeptides. To that end, experiments were carried out wherein two nonamers were tested, which were based upon the decapeptide which did give positive results. Specifically, either the first or tenth amino acid was omitted to create two peptides, i.e.:

Met Leu Leu Ala Val Leu Tyr Cys Leu (SEQ ID NO: 4)

Leu Leu Ala Val Leu Tyr Cys Leu Leu (SEQ ID NO: 5).

These peptides were tested in the same way the decapeptide was tested, as set forth in the prior examples at concentrations ranging from 10 μM to 1 nM. Three presenting cells were used. As summarized in Table 5, which follows, "T2" is a mutant human cell line, "CEMX721.174T2" as described by Salter, Immunogenetics 21: 235(1985). This line presents HLA-A2. "G2.2" is a variant of the cell line MZ2-MEL. The variant has been transfected with a gene coding for HLA-A2. The abbreviation "G2.2.5" stands for a variant which does not express HLA-A2. All cells were incubated with monoclonal antibody MA2.1 prior to contact with the cytolytic T cell clone. This procedure stabilizes so-called "empty" MHC molecules, although the mechanism by which this occurs is not well understood and effector CTLs 210/5 and 210/9 were both used. The results are set forth in Table 5, which follows. They show that at a concentration of 10 μM, the nonamer of SEQ ID NO: 4 was twice as effective when used with CTL clone 210/5, and four times as effective with clone 210/9 whereas the nonamer of SEQ ID NO: 5 was ineffective at inducing lysis.

Example 12

In further experiments, chromium release assays were carried out using the peptides of SEQ ID NOS: 4 and 5, as well as SEQ ID NO: 2. The target cells were allogeneic melanoma cells, i.e., MZ2-MEL, previously transfected with HLA-A2, and cell line T2, which presents HLA-A2, but has an antigen processing defect which results in an increased capacity to present exogenous peptides (Cerundolo et al., Nature 345: 449 (1990)). All cells were pretreated with monoclonal antibody MA2.1 for fifty minutes. The cells were incubated with the peptide of choice, for 30 minutes, at various concentrations. Then, one of CTL clones 210/9 and ISVB was added in an effector: target ratio of 60. Chromium release was measured after four hours, in the manner described supra.

Figure 7F:
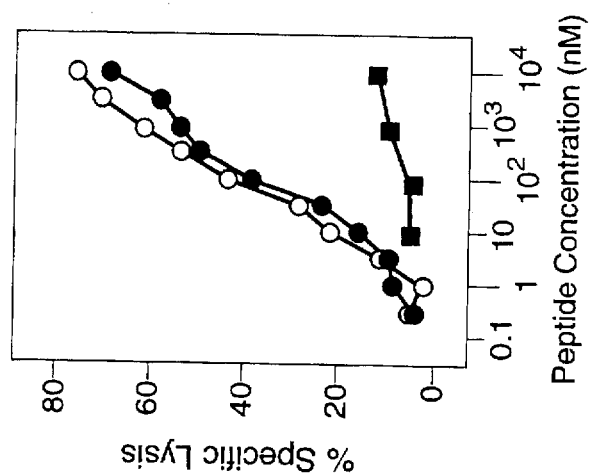
FIG. 7 shows, collectively, a series of chromium release assays using peptides described in this application on three different cell lines.
FIG. 7A presents experiments where the peptide of SEQ ID NO: 4 was used.
FIG. 7B shows results where the peptide of SEQ ID NO: 5 was used.
FIG. 7C sets forth results obtained using SEQ ID NO: 2.
Figure 7E:
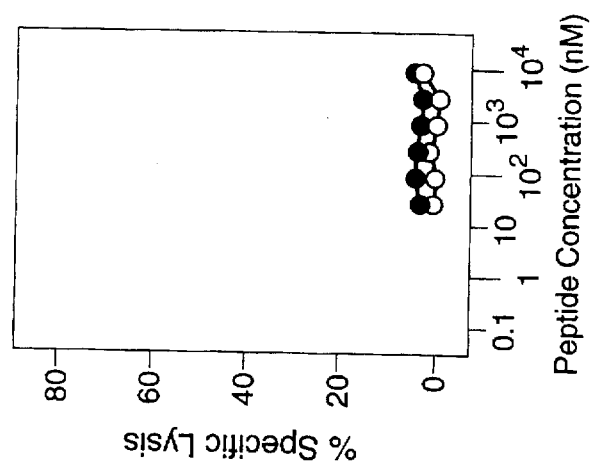
Figure 7D:
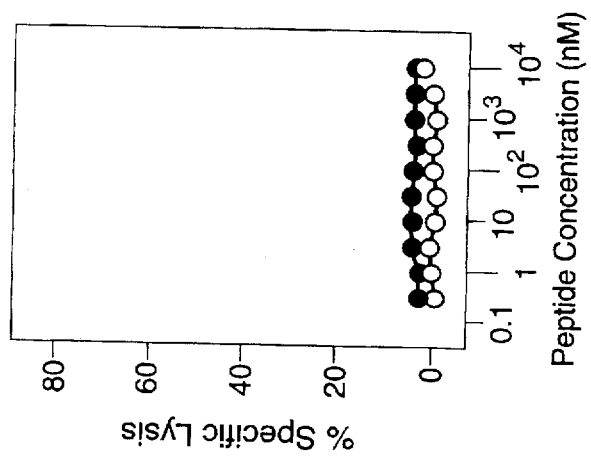

The results are presented in FIG. 7, i.e., FIGS. 7A–7C. The peptide of SEQ ID NO: 4 sensitized cells to CTL 210/9, while SEQ ID NO: 5 did not. SEQ ID NO: 2 sensitized cells to CTL IVSB, as already noted in previous examples.

TABLE 5

| 1 Effecteur | 2 Peptide | 3 Dose | 4 T2 + a − A2 | 5 G 2.2 + a − A2 | 6 G2.2.5 + a − A2 | 7 Effecteur | 8 | 9 Peptide | 10 Dose | 11 T2 + a − A2 | 12 G 2.2 + a − A2 | 13 G2.2.5 + a − A2 |
|---|---|---|---|---|---|---|---|---|---|---|---|---|
| 1 DAGI 210/5 | MLLAVLYCLL | 10 μM | 50 | 32 | 3 | | SK29 IVSB | MLLAVLYCLL | 10 μM | 3 | 3 | 7 |
| 2 50:1 | (LAUS 17-5) | 3 | 45 | 32 | 5 | | 60:1 | (LAUS 17-5) | 3 | 0 | 2 | 7 |

TABLE 5-continued

| 1 Effecteur | 2 Peptide | 3 Dose | 4 T2+ a-A2 | 5 G 2.2+ a-A2 | 6 G2.2.5+ a-A2 | 8 | 7 Effecteur | 9 Peptide | 10 Dose | 11 T2+ a-A2 | 12 G 2.2+ a-A2 | 13 G2.2.5+ a-A2 |
|---|---|---|---|---|---|---|---|---|---|---|---|---|
| 3 | | 1 | 39 | 26 | 3 | | | | 1 | 2 | 3 | 4 |
| 4 | | 300 nM | 33 | 18 | 4 | | | | 300 nM | 3 | 1 | 6 |
| 5 | | 100 | 24 | 8 | 5 | | | | 100 | 1 | 2 | 7 |
| 6 | | 30 | 13 | 5 | 5 | | | | 30 | 1 | 4 | 7 |
| 7 | | 10 | 6 | 5 | 5 | | | | 10 | 0 | 3 | 7 |
| 8 | | 3 | 2 | 2 | 4 | | | | 3 | 2 | 4 | 7 |
| 9 | | 1 | 2 | 1 | 3 | | | | 1 | 2 | 4 | 6 |
| 10 | | 300 pg | 1 | 4 | 3 | | | | 300 pg | 1 | 4 | 7 |
| 11 | | | | | | | | | | | | |
| 12 | MLLAVLYCL | 10 μM | 98 | 65 | 7 | | | MLLAVLYCL | 10 μM | 2 | 3 | 6 |
| 13 | (LAUS 19-5) | 3 | 87 | 60 | 4 | | | (LAUS 19-5) | 3 | 1 | 4 | 6 |
| 14 | | 1 | 95 | 66 | 5 | | | | 1 | 0 | 4 | 6 |
| 15 | | 300 nM | 95 | 60 | 3 | | | | 300 nM | 1 | 3 | 7 |
| 16 | | 100 | 91 | 56 | 3 | | | | 100 | 1 | 4 | 6 |
| 17 | | 30 | 87 | 48 | 3 | | | | 30 | 0 | 4 | 6 |
| 18 | | 10 | 82 | | 6 | | | | 10 | 0 | 4 | 6 |
| 19 | | 3 | 78 | | 4 | | | | 3 | 1 | 4 | 6 |
| 20 | | 1 | 76 | | 5 | | | | 1 | 1 | 3 | 8 |
| 21 | | 300 pg | 78 | | 5 | | | | 300 pg | 0 | 3 | 6 |
| 22 | | | | | | | | | | | | |
| 23 | LLAVLYCLL | 10 μM | 0 | 1 | 3 | | | LLAVLYCLL | 10 μM | 3 | 6 | 7 |
| 24 | (Laus 19-10) | 3 | 0 | 2 | 4 | | | (Laus 19-10) | 3 | 0 | 3 | 7 |
| 25 | | 1 | 3 | 3 | 3 | | | | 1 | 1 | 3 | 6 |
| 26 | | 300 nM | 0 | 2 | 4 | | | | 300 nM | 2 | 3 | 6 |
| 27 | | 100 | 1 | 2 | 4 | | | | 100 | 1 | 5 | 5 |
| 28 | | 30 | 1 | 1 | 2 | | | | 30 | 1 | 4 | 10 |
| 29 | | | | | | | | | | | | |
| 30 | YMNGTMSQV | 10 μM | 4 | 3 | 4 | | | YMNGTMSQV | 10 μM | 78 | 69 | 8 |
| 31 | (MAINZ) | 3 | 4 | 1 | 5 | | | (MAINZ) | 3 | 73 | 60 | 4 |
| 32 | | 1 | 2 | 2 | 4 | | | | 1 | 62 | 55 | 7 |
| 33 | | 300 nM | 1 | 3 | 2 | | | | 300 nM | 56 | 51 | 6 |
| 34 | | 100 | 0 | 1 | 6 | | | | 100 | 46 | 40 | 7 |
| 35 | | 30 | 0 | 2 | 4 | | | | 30 | 30 | 25 | 7 |
| 36 | | 10 | 0 | | 3 | | | | 10 | 23 | 18 | 8 |
| 37 | | 3 | 3 | | 3 | | | | 3 | 13 | 11 | 4 |
| 38 | | 1 | 2 | | 5 | | | | 1 | 3 | 9 | 5 |
| 39 | | | | | | | | | | 300 pg | 7 | 7 | 8 |
| 40 | | 0 | | 0 | 3 | 7 | | | | 100 | 4 | 7 | 7 |
| 41 | | | | | | | | | | 30 | 2 | 7 | 8 |
| 42 | DAGI 210/9 | MLLAVLYCLL | 10 μM | 26 | 23 | 8 | | | | | | | |
| 43 | 60:1 | (LAUS 17-5) | 3 | 20 | 23 | 6 | | | | 0 | 2 | 3 | 5 |
| 44 | | | 1 | 19 | 22 | 9 | | | | | | | |
| 45 | | | 300 nM | 13 | 16 | 7 | | spt. rel. | | | 184 | 441 | 195 |
| 46 | | | 100 | 10 | 9 | 6 | | max-spt | | | 1033 | 2522 | 1686 |
| 47 | | | 30 | 5 | 6 | 7 | | % | | | 15 | 15 | 10 |
| 48 | | | 10 | 3 | 4 | 6 | | | | | | | |
| 49 | | | 3 | 5 | 9 | 5 | | | | | | | |
| 50 | | | 1 | 7 | 3 | 6 | | | | | | | |
| 51 | | | 300 pg | 1 | 4 | 8 | | | | | | | |
| 52 | | | 100 | 1 | 3 | 8 | | | | | | | |
| 53 | | | 30 | 1 | 4 | 7 | | | | | | | |
| 54 | | | | | | | | | | | | | |
| 55 | | MLLAVLYCL | 10 μM | 98 | 82 | 12 | | | | | | | |
| 56 | | (LAUS 19-5) | 3 | 92 | 75 | 10 | | | | | | | |
| 57 | | | 1 | 89 | 74 | 6 | | | | | | | |
| 58 | | | 300 nM | 95 | 67 | 6 | | | | | | | |
| 59 | | | 100 | 87 | 63 | 6 | | | | | | | |
| 60 | | | 30 | 93 | 53 | 5 | | | | | | | |

Example 13

Work which followed up on the experiments set forth in example 10 was then carried out, in an effort to define the antigenic peptide presented by HLA-B44. To do so, cDNA sequences corresponding to fragments of the tyrosinase cDNA sequence were cotransfected, together with a gene coding for HLA-B44, into COS-7 cells. The protocol is essentially that described in example 6, supra. The cytolytic T cell clone 22/31, discussed supra, was used. TNF release was determined. Two fragments, i.e., base fragments 1–611, and 427–1134 induced TNF release. This suggested that the presented peptide was in the overlapping region. As a result of this observation, shorter fragments were tested. Fragments corresponding to nucleotides 574–831 and 385–612 were able to induce TNF release. These data suggest that a fragment corresponding to nucleotides 574–612 encoded the relevant peptide. As a result, the 13 amino acid peptide encoded for by nucleotides 574–612 was synthesized. This peptide was then used in experiments to determine whether it induced lysis by CTL 22/31. Table 6, which follows, shows that the 13-mer rendered two EBV transfected cell lines which express HLA-B44 sensitive to lysis.

TABLE 6

10F94-tyros 13-mer sur EBV-I

| 1<br>Effector | 2<br>Dose pept 13 A.A. | 3<br>Rosi – EBV | 4<br>MZ2 – EBV |
|---|---|---|---|
| 1 MZ2-CTL-22/31 | SEIWRDIDFAHEA | | |
| 2 | | | |
| 3  60:1 | 30 µM | 83 | 71 |
| 4 | 10 | 85 | 72 |
| 5 | 3 | 77 | 66 |
| 6 | 1 | 79 | 63 |
| 7 | 300 nM | 60 | 33 |
| 8 | 100 | 44 | 17 |
| 9 | 30 | 21 | 4 |
| 10 | 10 | 9 | 5 |
| 11 | 3 | 10 | 6 |
| 12 | | | |
| 13 | 0 | 10 | 6 |
| 14 | | | |
| 15 spt. rel. | | 393 | 472 |
| 16 max. rel. | | 1698 | 1792 |
| 17 % | | 23 | 26 |

As a follow up, even shorter peptides were tested. A decamer corresponding to nucleotide bases 574–604, i.e.

Ser Glu Ile Trp Arg Asp Ile Asp Phe Ala (SEQ ID NO: 6)

did provoke lysis, as did peptide:

Ser Glu Ile Trp Arg Asp Ile Asp Phe (SEQ ID NO: 7)

Figure 8A:
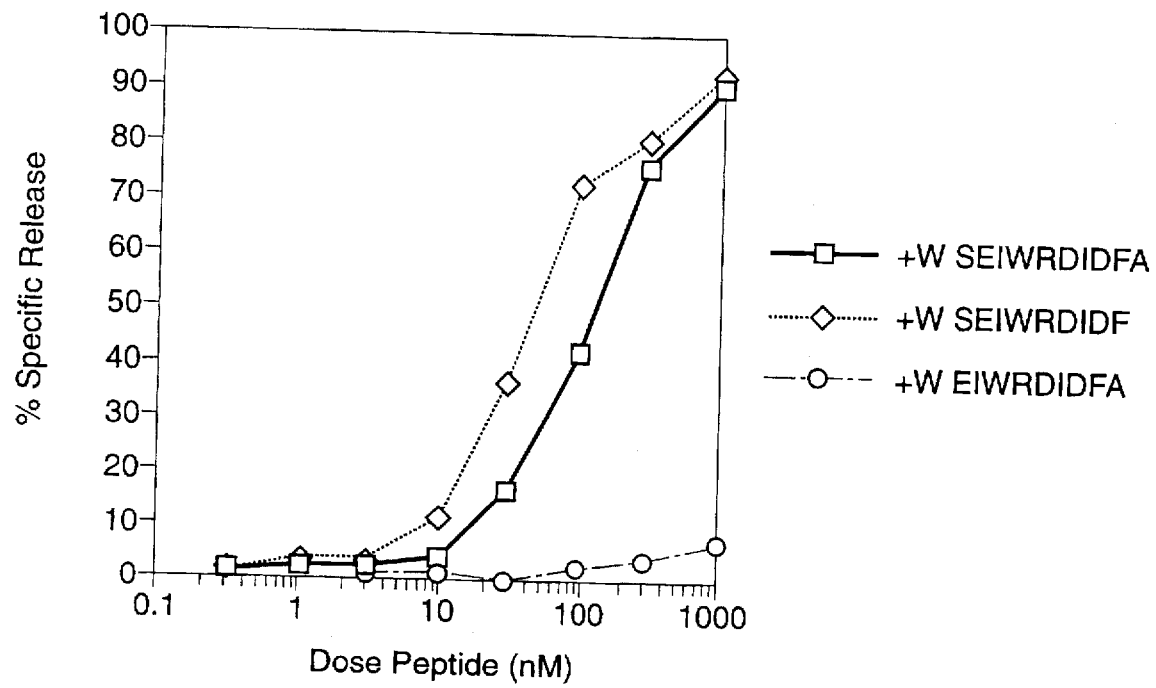
FIGS. 8A and 8B show work using a cell line which presents MHC molecule HLA-B44, and cytolytic T cell clone 22/31 ("CTL 22/31" hereafter).
Figure 8B:
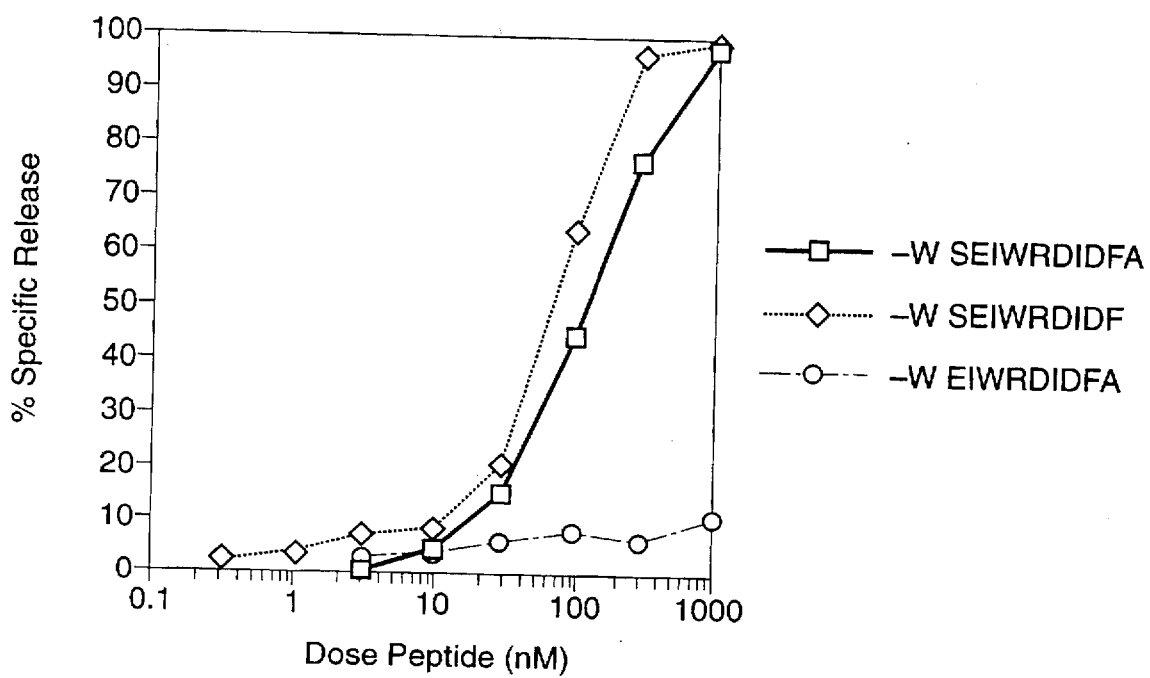

The nonamer:

Glu Ile Trp Arg Asp Ile Asp Phe Ala (SEQ ID NO: 8)

in contrast, was not recognized. Table 7, which follows, summarizes these results, which are also depicted in FIG. 8.

The only other peptide reported to be bound by HLA-B44 is

Glu Glu Asn Leu Leu Asp Phe Val Arg Phe (SEQ ID NO: 9)

as reported by Burrows et al., J. Virol 64: 3974 (1990). The data described supra suggest that Glu at second position and Phe in ninth position may represent anchor residues for HLA-B44.

sponding to N-terminal serine for SEQ ID NO: 7. Specifically, SK29-MEL tyrosinase consisted of ATG at positions 537–539, TCT at positions 575–577, and CAA at positions 1207. Kwon et al differ in that they show TAT at 575–577, while Bouchard, et al show ATC, TAT, and CGA at the listed positions. The change results in tyrosine being at the N-terminus rather than serine. As a result, tests were carried out, using SEQ ID NO: 10, i.e.

Tyr Glu Ile Trp Arg Asp Ile Asp Phe

According to Giebel et al., Nucl. Acids Res. 18: 3103 (1990), and Johnston et al., Nucl. Acids Res. 20: 143 (1992), this allele is present in about 50% of the caucasian population. It was important to determine if SEQ ID NO: 10 could sensitize CTLs.

Figure 9A:
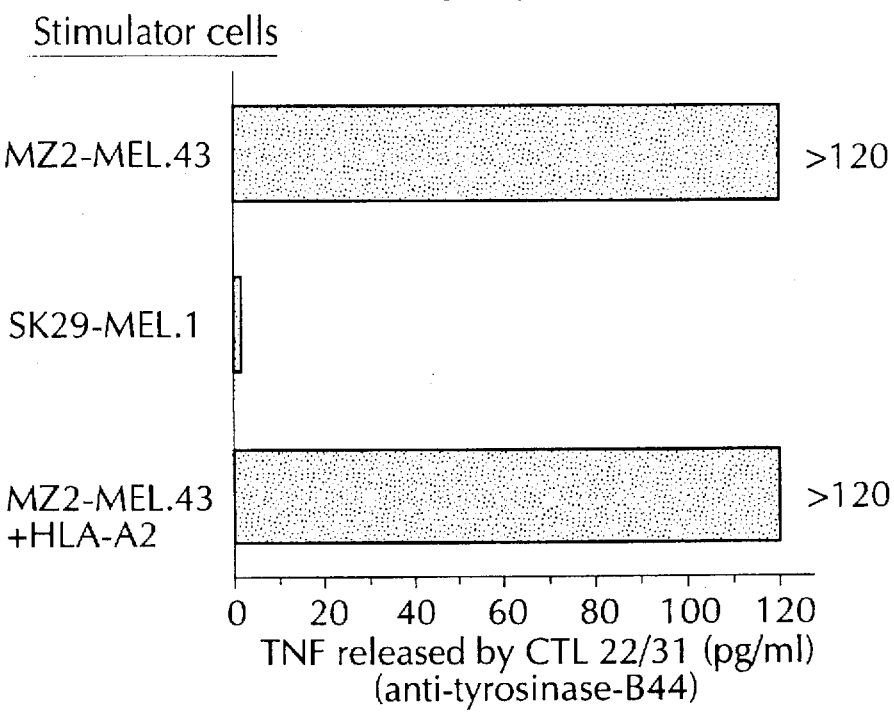
FIGS. 9A and 9B show results obtained when CTL clones 22/31 and IVSB were used on target cells which express HLA-A2 and/or HLA-B44 MHC molecules.
Figure 9B:
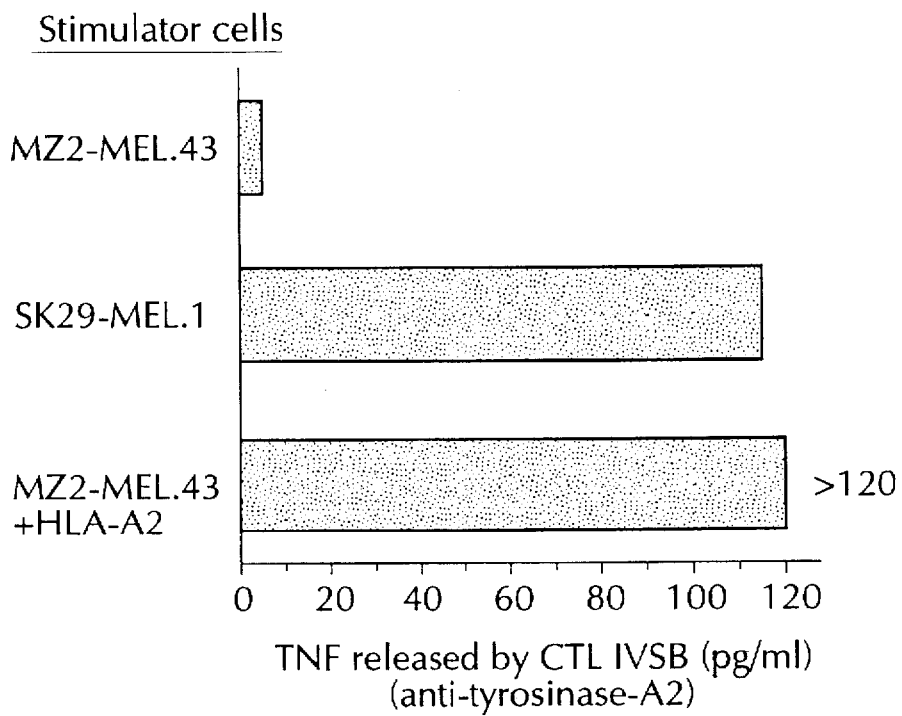

The peptide of SEQ ID NO: 10 was tested in the same manner discussed in examples 12 and 13, supra, using CTL 22/31. It was found that the amount of SEQ ID NO: 10 necessary to provoke 50% of maximal lysis by CTL 22/31 was approximately the same as that required for SEQ ID NO: 7. FIGS. 9A and 9B, which present some of these data, show results obtained when CTL 22/31 and CTL IVSB were used on target cells which express, simultaneously, HLA-A2 and HLA-B44. The line MZ2-MEL.43 expresses HLA-B44, but not HLA-A2. The line SK29-MEL.1 tests positive for both HLA-B44 and HLA-A2. The line referred to as "MZ2-MEL.43+HLA-A2" is an MZ2-MEL.43 cell, transfected with DNA encoding HLA-A*0201 , One interesting feature of these results is the fact that CTL22/31 did not recognize SK29-MEL.1 stimulated cells, while CTL IVSB did so (and did not recognize MZ2-MEL.43). This observation led to the next experiments.

Example 15

A further CTL clone, i.e., CTL clone 329B/5. was also derived, albeit somewhat differently than the two CTL clones discussed supra.

In order to derive CTL clone 329B/5, adherent cells from peripheral mononuclear cells (autologous macrophages and dendritic cells) of a healthy, HLA-B*4402 positive individual were grown for one week in RPMI medium, supplemented with 10% fetal calf serum ("FCS"), IL-4 (50 U/ml), and GM-CSF (100 ng/ml). The cells were then pulsed with the peptide of SEQ ID NO: 7, disclosed supra, (50 µM) for

TABLE 7

10M94-pept tyros on B44

| 1<br>Effector | 2<br>Dose | 3<br>+W SEIWRDIDFA | 4<br>+W SEIWRDIDF | 5<br>+W EIWRDIDFA | 6<br>–W SEIWRDIDFA | 7<br>+W SEIWRDIDF | 8<br>–W EIWRDIDFA |
|---|---|---|---|---|---|---|---|
| 1 MZ2-CTL-22/31 | 1 µM | 91 | 93 | 7 | 98 | 99 | 11 |
| 2 | 300 nM | 76 | 81 | 4 | 77 | 97 | 6 |
| 3  45:1 | 100 | 43 | 73 | 2 | 45 | 64 | 8 |
| 4 | 30 | 17 | 37 | 0 | 15 | 21 | 6 |
| 5 | 10 | 4 | 12 | 1 | 5 | 8 | 4 |
| 6 | 3 | 3 | 4 | 1 | 0 | 7 | 2 |
| 7 | 1 | 2 | 4 | | | 3 | |
| 8 | 0.3 | 1 | 1 | | | 2 | |

Example 14

As reported in Example 5, supra, the cDNA for tyrosinase which was isolated from SK29-MEL was nearly identical to the previously identified tyrosinase cDNA. There were three differences in all, one of which was in the codon correfour hours, in the presence of β2 microglobulin (2.5 ug/ml). The adherent cells were irradiated, and two million CD8+ sorted T lymphocytes were added in a final volume of 2 ml of Iscove's medium supplemented with 10% human serum, 1000 U/ml of IL-6, and 5 ng/ml of IL-12. Responder cells were stimulated on days 7 and 14 with adherent cells which had been pulsed with SEQ ID NO: 7, in medium supplemented with 10 U/ml of IL-2 and 5 ng/ml of IL-7. On day 21, responder lymphocytes were cloned by limiting dilution in microwells containing HLA-B44 positive irradiated LB33-MEL.A cells ($10^4$ cells per microwell), which had been pulsed with SEQ ID NO:8 (1 µM), and $2\times10^4$ irradiated LG2-EBV lymphoblastoid cells, which acted as feeder cells.

Microcultures were stimulated every seven days, following the same procedure.

After five weeks, CTL clone 329B/5 was grown in 24 wells, and was stimulated, weekly, with $2\times10^5$ irradiated LB33-MEL.A cells which had been pulsed with SEQ ID NO: 7, and $10^6$ irradiated LG2-EBV cells, in medium supplemented with IL-2 (50 U/ml) and IL-4 (5 U/ml).

CTL clone 329B/5 was used in several of the experiments presented infra.

Example 16

One possible reason for the results in example 14 was a difference in HLA subtype It is known that there are two major subtypes for HLA-B44, i.e., HLA-B*4402 and HLA-B*4403. Melanoma cell line SK29-MEL expresses HLA-B*4402, while MZ2-MEL expressed HLA-B*4403.

To examine this possibility, lymphoblastoid cell lines, taken from three different patients (LB17, LB33, and B12), and transformed by Epstein Barr virus (EBV), were used of both subtypes were pulsed with SEQ ID NO: 8, and then tested for sensitivity to lysis by CTL 22/31, also as described, supra. The CTL clone 329B/5 described in example 15 was also used.

Figure 10A:
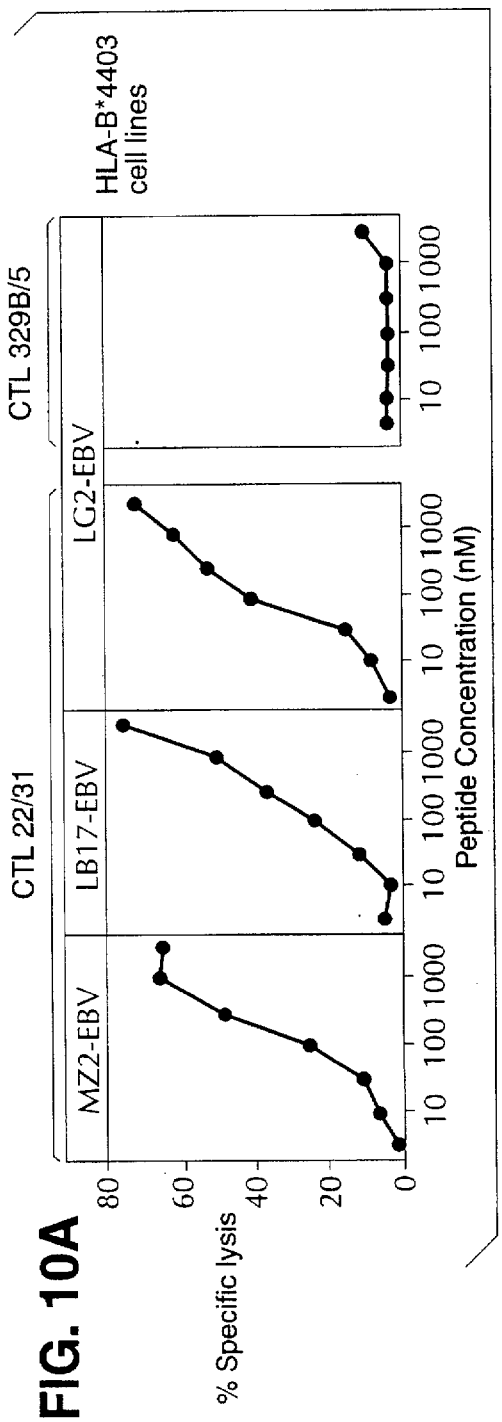
FIG. 10 depicts lysis studies using CTL clone 329B/5, which is specific for HLA-B*4402 cells, and CTL 22/31, which is specific for HLA-B*4403 cell lines.
Figure 10B:
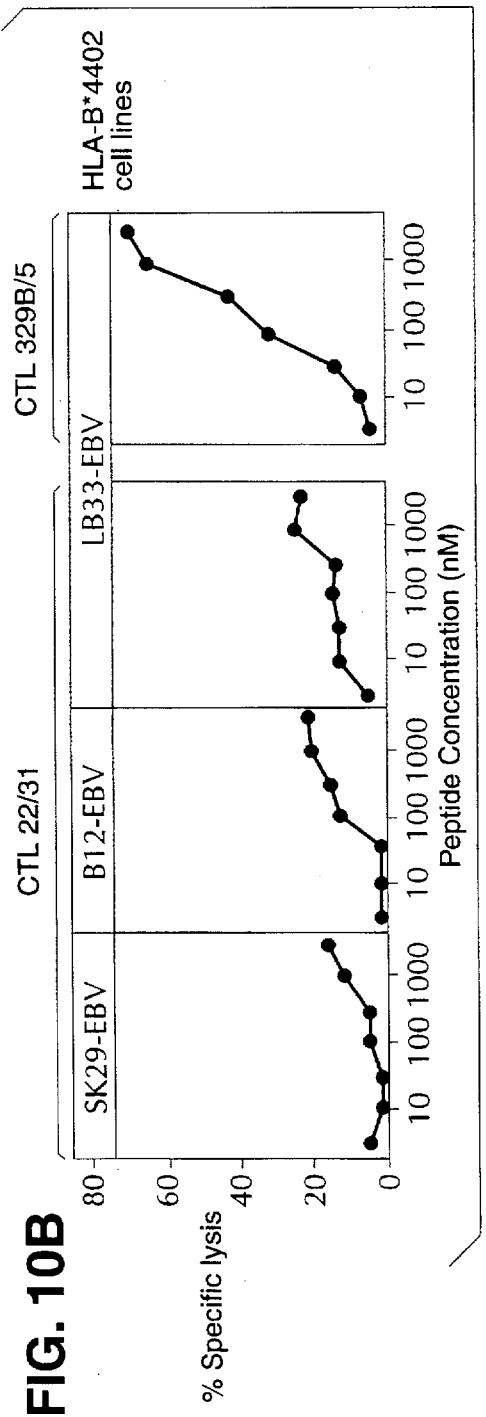

FIG. 10 shows the results of these experiments. All HLA-B*4403 positive cells were lysed very well by CTLs 22/31, while, little, if any lysis was observed on HLA-B*4402 lines when CTL 22/31 was used. The conclusion is that CTLs can differentiate between, and are restricted to, HLA subtypes.

Example 17

Additional experiments were also carried out to determine if SEQ ID NO: 7, which was shown to complex to HLA-B*4403 and then to stimulate CTLs, could also be presented by HLA-B*4402 cells.

Coulie et al., Proc. Natl. Acad. Sci. USA 92: 7976–7980 (1995) describe the peptide Glu Glu Lys Leu Ile Val Val Leu Phe (SEQ ID NO: 11) as one which binds to HLA-B*4402 molecules. The peptide of SEQ ID NO: 10 did compete effectively with SEQ ID NO: 11, showing that it did, in fact, bind to HLA-B*4402 molecules.

Example 18

Figure 11:
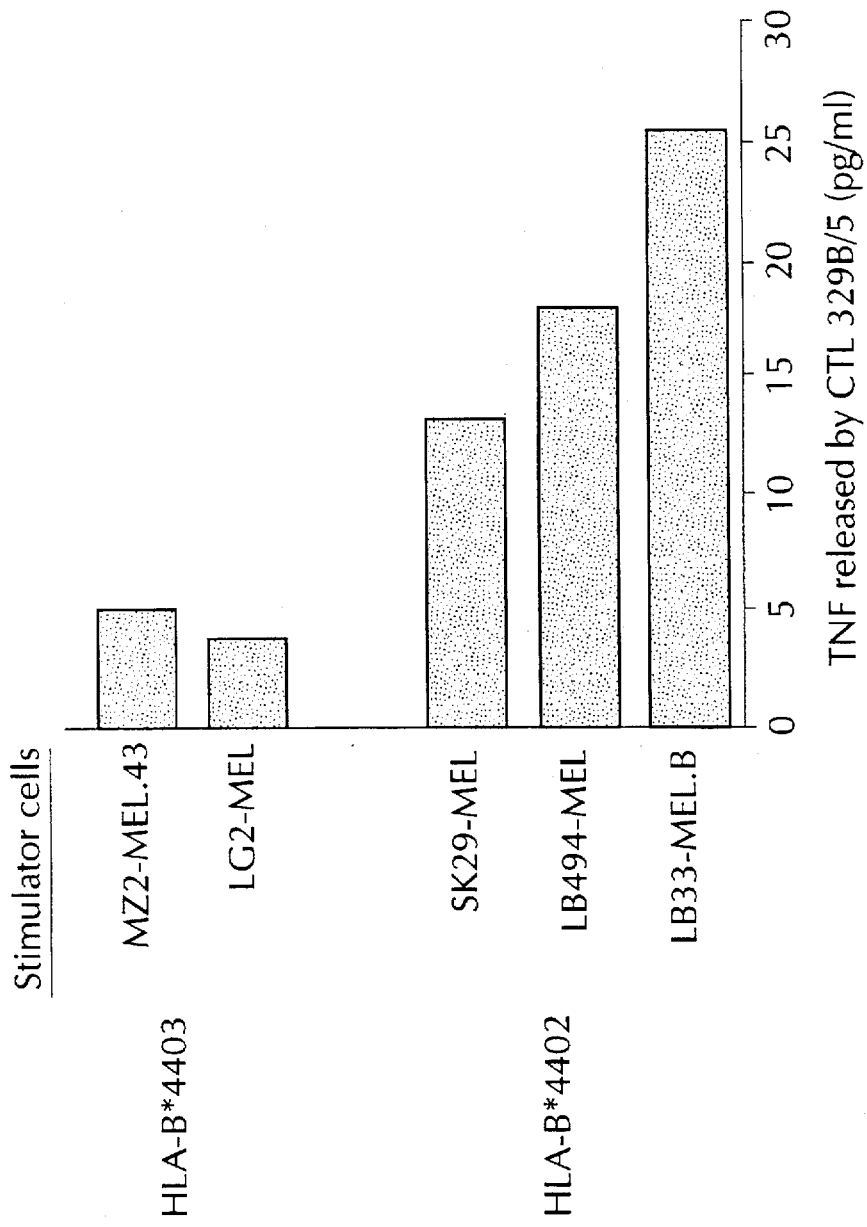
FIG. 11 sets forth the results of experiments involving stimulation of TNF release in assays involving CTL 329B/5. They show that the CTL clone 329B/5 is highly specific for HLA-B*4402 presenting cells.

CTL clone 329B/5 was tested in lysis assays, of the type discussed supra. Two HLA-B*4403 positive cell lines (MZ2-MEL.43 and LG2-MEL), and three HLA-B'4402 positive cell lines (SK29-MEL, LB494-MEL, and LB33-MEL.B), were tested in TNF release assays. All cell lines expressed tyrosinase. Results are presented in FIG. 11. Note that stimulation of TNF release was much higher for the HLA-B*4402 melanoma cell lines.

Example 19

The fact that SEQ ID NO: 7 and SEQ ID NO: 10 both bound to HLA-B44 molecules and provoked lysis by CTLs suggested that the N-terminus was not a critical residue for binding to HLA-B44. Additional studies were carried out to determine if other residues were critical.

In these experiments, peptides were synthesized wherein one of the amino acids in each of the nine positions of SEQ ID NO: 7 was substituted by alanine. Then, C1R-B4403 cells were chromium labelled for one hour at 37° C., in the presence of anti-MHC class I antibody W6/32 (30% v/v culture medium of hybridoma cells), and washed. Labelled cells (1000 per well), were incubated with various concentrations of peptide, for 30 minutes at 20° C. Then CTL 22/31 was added, at an E:T (effector:target) ratio of 10:1. Chromium release was measured after four hours.

The results which follow are presented as relative antigenic activity. This is calculated as the concentration of unsubstituted peptide required to obtain 50% maximal lysis, divided by concentration of the variant peptide needed to secure 50% maximal lysis. For the unsubstituted peptide, SEQ ID NO: 8, 50% maximal lysis was obtained at 3 nM.

The results indicate that every amino acid in the peptide except for position 1 was required for recognition.

| PEPTIDE | RELATIVE ANTIGENIC ACTIVITY |
|---|---|
| Ser Glu Ile Trp Arg Asp Ile Asp Phe (SEQ ID NO: 7) | 1 |
| Ala | 1 |
| Ala | 0 |
| Ala | 0.066 |
| Ala | 0 |
| Ala | 0 |
| Ala | 0 |
| Ala | 0 |
| Ala | 0.15 |
| Ala | 0 |

The foregoing experiments demonstrate that tyrosinase is processed as a tumor rejection antigen precursor, leading to formation of complexes of the resulting tumor rejection antigens with a molecule on at least some abnormal cells, for example, melanoma cells with HLA-A2 or HLA-B44 phenotype. These tumor rejection antigens may be represented by the formula Xaa Glu Ile Trp Arg Asp Ile Asp Phe (SEQ ID NO: 12), wherein Xaa is any amino acid. Such an antigen, where Xaa is serine, was disclosed in the parent application and is thus not a part of the invention as claimed herein Specific antigens, wherein Xaa is Tyr or Ala, are specifically disclosed herein. The complex can be recognized by CTLs, and the presenting cell lysed. This observation has therapeutic and diagnostic ramifications which are features of the invention. With respect to therapies, the observation that CTLs which are specific for abnormal cells presenting the aforementioned complexes are produced, suggests various therapeutic approaches. One such approach is the administration of CTLs specific to the complex to a subject with abnormal cells of the phenotype at issue. It is within the skill of the artisan to develop such CTLs in vitro. Specifically, a sample of cells, such as blood cells, are contacted to a cell presenting the complex and are capable of provoking a specific CTL to proliferate. The target cell can be a transfectant, such as a COS cell of the type described supra. These transfectants present the desired complex on their surface and, when combined with a CTL of interest, stimulate its proliferation. So as to enable the artisan to produce these CTLs, vectors containing the genes of interest, i.e., pcDNA-1/Ampl (HLA-A2), and p123.B2 (human tyrosinase), have been deposited in accordance with the Budapest Treaty at the Institut Pasteur, under Accession Numbers I1275 and I1276, respectively. COS cells, such as those used herein are widely available, as are other suitable host cells.

To detail the therapeutic methodology, referred to as adoptive transfer (Greenberg, J. Immunol. 136(5): 1917 (1986); Reddel et al., Science 257: 238 (Jul. 10, 1992); Lynch et al., Eur. J. Immunol. 21: 1403–1410 (1991); Kast et al., Cell 59: 603–614 (Nov. 17, 1989)), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present one or more of the HLA/tyrosinase derived peptide complexes. This can be determined very easily. For example CTLs are identified using the transfectants discussed supra, and once isolated, can be used with a sample of a subject's abnormal cells to determine lysis in vitro. If lysis is observed, then the use of specific CTLs in such a therapy may alleviate the condition associated with the abnormal cells. A less involved methodology examines the abnormal cells for their HLA phenotype, using standard assays, and determines expression of tyrosinase via amplification using, e.g., PCR. The fact that a plurality of different HLA molecules present TRAs derived from tyrosinase increases the number of individuals who are suitable subjects for the therapies discussed herein.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., Proc. Natl. Acad. Sci. USA 88: 110–114 (January, 1991) exemplifies this approach, showing the use of transfected cells expressing HPVE7 peptides in a therapeutic regime. Various cell types may be used. Similarly, vectors carrying one or both of the genes of interest may be used. Viral or bacterial vectors are especially preferred. In these systems, the gene of interest is carried by, e.g., a Vaccinia virus or the bacteria BCG, and the materials de facto "infect" host cells. The cells which result present the complex of interest, and are recognized by autologous CTLs, which then proliferate. A similar effect can be achieved by combining tyrosinase itself with an adjuvant to facilitate incorporation into HLA-A2 presenting cells. The enzyme is then processed to yield the peptide partner of the HLA molecule.

The foregoing discussion refers to "abnormal cells" and "cellular abnormalities". These terms are employed in their broadest interpretation, and refer to any situation where the cells in question exhibit at least one property which indicates that they differ from normal cells of their specific type. Examples of abnormal properties include morphological and biochemical changes, e.g. Cellular abnormalities include tumors, such as melanoma, autoimmune disorders, and so forth.

The invention also provides a method for identifying precursors to CTL targets. These precursors are referred to as tumor rejection antigens when the target cells are tumors, but it must be pointed out that when the cell characterized by abnormality is not a tumor, it would be somewhat misleading to refer to the molecule as a tumor rejection antigen. Essentially, the method involves identifying a cell which is the target of a cytolytic T cell of the type discussed supra. Once such a cell is identified, total RNA is converted to a cDNA library, which is then transfected into a cell sample capable of presenting an antigen which forms a complex with a relevant HLA molecule. The transfectants are contacted with the CTL discussed supra, and again, targeting by the CTL is observed (lysis and/or TNF production). These transfectants which are lysed are then treated to have the cDNA removed and sequenced, and in this manner a precursor for an abnormal condition, such as a tumor rejection antigen precursor, can be identified.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method for identifying a subject for treatment with a therapeutic agent which is specific for complexes of an HLA-B44 molecule and a peptide of formula Xaa Glu Ile Trp Arg Asp Ile Asp Phe (SEQ ID. NO: 12) wherein Xaa is any amino acid but serine, and wherein said complexes are present on surfaces of abnormal cells of said subject, comprising (i) contacting a sample containing abnormal cells, which has been taken from said subject, with a cytolytic T cell specific for said complexes, and
   (ii) determining lysis of at least some of said abnormal cells as an indication that the subject is a candidate for said treatment.

2. The method of claim 1, wherein said MHC molecule is HLA-B*4402.

3. The method of claim 1, wherein said MHC molecule is HLA-B*4403.

4. Method for treating a cellular abnormality comprising administering to a subject with a cellular abnormality characterized by presentation of complexes of an HLA-B44 molecule and a peptide of formula Xaa Glu Ile Trp Arg Asp Ile Asp Phe, (SEQ ID NO: 12) wherein Xaa is any amino acid but serine on surfaces of abnormal cells an amount of cytolytic T cells specific for said complexes sufficient to lyse said abnormal cells.

5. The method of claim 4, wherein said cytolytic T cells are autologous.

6. Isolated cytolytic T cell specific for a complex of an HLA-B44 molecule and a peptide of formula Xaa Glu Ile Trp Arg Asp Ile Asp Phe, (SEQ ID NO: 12) wherein said Xaa is any amino acid but serine.

7. A method for identifying abnormal cells which present complexes of an HLA-B44 molecule and a peptide of formula Xaa Glu Ile Trp Arg Asp Ile Asp Phe (SEQ ID NO: 12) wherein Xaa is any amino acid but serine on their surfaces, comprising contacting a sample which contains said abnormal cells with a cytolytic T cell specific for said complex and determining lysis of said abnormal cells by said cytolytic T cells as a determination of said abnormal cells.

8. Isolated peptide of formula Xaa Glu Ile Trp Arg Asp Ile Asp Phe, (SEQ ID NO: 12) wherein Xaa is any amino acid but serine.

9. The isolated peptide of claim 8, wherein Xaa is Tyr.

10. The isolated peptide of claim 8, wherein Xaa is Ala.

* * * * *

UNITED STATES PATENT AND TRADEMARK OFFICE
CERTIFICATE OF CORRECTION

PATENT NO. : 5,744,316
DATED : Apr. 28, 1998
INVENTOR(S) : Lethe et al.

It is certified that error appears in the above-identified patent and that said Letters Patent is hereby corrected as shown below:

[75] Inventors: Bernard Lethe; Vincent Brichard; Aline Van Pel, all of Brussels, Belgium; Thomas Wölfel, Mainz, Germany; Thierry Boon-Falleur, Brussels, Belgium".

In column 7, line 55, change "370°C" to -- 37°C --.
In column 8, Table 4, in the caption of the fourth column, change "NAB-MEL*" to -- NA8-MEL* --.
In columns 13-14, Table 7, in the caption of the seventh column, change plus sign "+" to minus sign -- - --.
In column 15, line 29, change "SEQ ID NO: 8" to -- SEQ ID NO: 7 --.
In column 15, line 57, change "B ' 4402" to -- B*4402 --.

Signed and Sealed this

Twenty-second Day of August, 2000

Q. TODD DICKINSON

Attest:

Attesting Officer

Director of Patents and Trademarks

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
( A ) LENGTH: 1906 base pairs
( B ) TYPE: nucleic acid
( C ) STRANDEDNESS: single
( D ) TOPOLOGY: linear ( x i ) SEQUENCE DESCRIPTION: SEQ ID NO: 1:

```
GACCTTGTGA GGACTAGAGG AAGA ATG CTC CTG GCT GTT TTG TAC TGC CTG        51
                            Met Leu Leu Ala Val Leu Tyr Cys Leu
                                             5

CTG TGG AGT TTC CAG ACC TCC GCT GGC CAT TTC CCT AGA GCC TGT GTC        99
```

| | | | | | | | | | | | | | | | |
|---|---|---|---|---|---|---|---|---|---|---|---|---|---|---|---|
| Leu | Trp | Ser | Phe | Gln | Thr | Ser | Ala | Gly | His | Phe | Pro | Arg | Ala | Cys | Val |
| 10 | | | | 15 | | | | | 20 | | | | | 25 | |

```
TCC TCT AAG AAC CTG ATG GAG AAG GAA TGC TGT CCA CCG TGG AGC GGG      147
Ser Ser Lys Asn Leu Met Glu Lys Glu Cys Cys Pro Pro Trp Ser Gly
            30                  35                  40

GAC AGG AGT CCC TGT GGC CAG CTT TCA GGC AGA GGT TCC TGT CAG AAT      195
Asp Arg Ser Pro Cys Gly Gln Leu Ser Gly Arg Gly Ser Cys Gln Asn
                45                  50                  55

ATC CTT CTG TCC AAT GCA CCA CTT GGG CCT CAA TTT CCC TTC ACA GGG      243
Ile Leu Leu Ser Asn Ala Pro Leu Gly Pro Gln Phe Pro Phe Thr Gly
            60                  65                  70

GTG GAT GAC CGG GAG TCG TGG CCT TCC GTC TTT TAT AAT AGG ACC TGC      291
Val Asp Asp Arg Glu Ser Trp Pro Ser Val Phe Tyr Asn Arg Thr Cys
    75                  80                  85

CAG TGC TCT GGC AAC TTC ATG GGA TTC AAC TGT GGA AAC TGC AAG TTT      339
Gln Cys Ser Gly Asn Phe Met Gly Phe Asn Cys Gly Asn Cys Lys Phe
90                  95                  100                 105

GGC TTT TGG GGA CCA AAC TGC ACA GAG AGA CGA CTC TTG GTG AGA AGA      387
Gly Phe Trp Gly Pro Asn Cys Thr Glu Arg Arg Leu Leu Val Arg Arg
                110                 115                 120

AAC ATC TTC GAT TTG AGT GCC CCA GAG AAG GAC AAA TTT TTT GCC TAC      435
Asn Ile Phe Asp Leu Ser Ala Pro Glu Lys Asp Lys Phe Phe Ala Tyr
            125                 130                 135

CTC ACT TTA GCA AAG CAT ACC ATC AGC TCA GAC TAT GTC ATC CCC ATA      483
Leu Thr Leu Ala Lys His Thr Ile Ser Ser Asp Tyr Val Ile Pro Ile
            140                 145                 150

GGG ACC TAT GGC CAA ATG AAA AAT GGA TCA ACA CCC ATG TTT AAC GAC      531
Gly Thr Tyr Gly Gln Met Lys Asn Gly Ser Thr Pro Met Phe Asn Asp
    155                 160                 165

ATC AAT ATT TAT GAC CTC TTT GTC TGG ATG CAT TAT TAT GTG TCA ATG      579
Ile Asn Ile Tyr Asp Leu Phe Val Trp Met His Tyr Tyr Val Ser Met
170                 175                 180                 185

GAT GCA CTG CTT GGG GGA TCT GAA ATC TGG AGA GAC ATT GAT TTT GCC      627
Asp Ala Leu Leu Gly Gly Ser Glu Ile Trp Arg Asp Ile Asp Phe Ala
            190                 195                 200

CAT GAA GCA CCA GCT TTT CTG CCT TGG CAT AGA CTC TTC TTG TTG CGG      675
His Glu Ala Pro Ala Phe Leu Pro Trp His Arg Leu Phe Leu Leu Arg
            205                 210                 215

TGG GAA CAA GAA ATC CAG AAG CTG ACA GGA GAT GAA AAC TTC ACT ATT      723
Trp Glu Gln Glu Ile Gln Lys Leu Thr Gly Asp Glu Asn Phe Thr Ile
            220                 225                 230

CCA TAT TGG GAC TGG CGG GAT GCA GAA AAG TGT GAC ATT TGC ACA GAT      771
Pro Tyr Trp Asp Trp Arg Asp Ala Glu Lys Cys Asp Ile Cys Thr Asp
    235                 240                 245

GAG TAC ATG GGA GGT CAG CAC CCC ACA AAT CCT AAC TTA CTC AGC CCA      819
Glu Tyr Met Gly Gly Gln His Pro Thr Asn Pro Asn Leu Leu Ser Pro
250                 255                 260                 265

GCA TCA TTC TTC TCC TCT TGG CAG ATT GTC TGT AGC CGA TTG GAG GAG      867
Ala Ser Phe Phe Ser Ser Trp Gln Ile Val Cys Ser Arg Leu Glu Glu
            270                 275                 280

TAC AAC AGC CAT CAG TCT TTA TGC AAT GGA ACG CCC GAG GGA CCT TTA      915
Tyr Asn Ser His Gln Ser Leu Cys Asn Gly Thr Pro Glu Gly Pro Leu
            285                 290                 295

CGG CGT AAT CCT GGA AAC CAT GAC AAA TCC AGA ACC CCA AGG CTC CCC      963
Arg Arg Asn Pro Gly Asn His Asp Lys Ser Arg Thr Pro Arg Leu Pro
            300                 305                 310

TCT TCA GCT GAT GTA GAA TTT TGC CTG AGT TTG ACC CAA TAT GAA TCT      1011
Ser Ser Ala Asp Val Glu Phe Cys Leu Ser Leu Thr Gln Tyr Glu Ser
    315                 320                 325

GGT TCC ATG GAT AAA GCT GCC AAT TTC AGC TTT AGA AAT ACA CTG GAA      1059
```

| | | | | | | | | | | | | | | | | |
|---|---|---|---|---|---|---|---|---|---|---|---|---|---|---|---|---|
| | Gly<br>330 | Ser | Met | Asp | Lys<br>335 | Ala | Ala | Asn | Phe | Ser<br>340 | Phe | Arg | Asn | Thr | Leu | Glu<br>345 |
| GGA<br>Gly | TTT<br>Phe | GCT<br>Ala | AGT<br>Ser | CCA<br>Pro<br>350 | CTT<br>Leu | ACT<br>Thr | GGG<br>Gly | ATA<br>Ile | GCG<br>Ala<br>355 | GAT<br>Asp | GCC<br>Ala | TCT<br>Ser | CAA<br>Gln | AGC<br>Ser<br>360 | AGC<br>Ser | 1107 |
| ATG<br>Met | CAC<br>His | AAT<br>Asn | GCC<br>Ala<br>365 | TTG<br>Leu | CAC<br>His | ATC<br>Ile | TAT<br>Tyr | ATG<br>Met<br>370 | AAT<br>Asn | GGA<br>Gly | ACA<br>Thr | ATG<br>Met | TCC<br>Ser<br>375 | CAG<br>Gln | GTA<br>Val | 1155 |
| CAG<br>Gln | GGA<br>Gly | TCT<br>Ser<br>380 | GCC<br>Ala | AAC<br>Asn | GAT<br>Asp | CCT<br>Pro | ATC<br>Ile<br>385 | TTC<br>Phe | CTT<br>Leu | CTT<br>Leu | CAC<br>His | CAT<br>His<br>390 | GCA<br>Ala | TTT<br>Phe | GTT<br>Val | 1203 |
| GAC<br>Asp | AGT<br>Ser<br>395 | ATT<br>Ile | TTT<br>Phe | GAG<br>Glu | CAG<br>Gln | TGG<br>Trp<br>400 | CTC<br>Leu | CAA<br>Gln | AGG<br>Arg | CAC<br>His | CGT<br>Arg<br>405 | CCT<br>Pro | CTT<br>Leu | CAA<br>Gln | GAA<br>Glu | 1251 |
| GTT<br>Val<br>410 | TAT<br>Tyr | CCA<br>Pro | GAA<br>Glu | GCC<br>Ala<br>415 | AAT<br>Asn | GCA<br>Ala | CCC<br>Pro | ATT<br>Ile | GGA<br>Gly<br>420 | CAT<br>His | AAC<br>Asn | CGG<br>Arg | GAA<br>Glu | TCC<br>Ser<br>425 | TAC<br>Tyr | 1299 |
| ATG<br>Met | GTT<br>Val | CCT<br>Pro | TTT<br>Phe | ATA<br>Ile<br>430 | CCA<br>Pro | CTG<br>Leu | TAC<br>Tyr | AGA<br>Arg | AAT<br>Asn<br>435 | GGT<br>Gly | GAT<br>Asp | TTC<br>Phe | TTT<br>Phe | ATT<br>Ile<br>440 | TCA<br>Ser | 1347 |
| TCC<br>Ser | AAA<br>Lys | GAT<br>Asp | CTG<br>Leu<br>445 | GGC<br>Gly | TAT<br>Tyr | GAC<br>Asp | TAT<br>Tyr | AGC<br>Ser<br>450 | TAT<br>Tyr | CTA<br>Leu | CAA<br>Gln | GAT<br>Asp | TCA<br>Ser<br>455 | GAC<br>Asp | CCA<br>Pro | 1395 |
| GAC<br>Asp | TCT<br>Ser | TTT<br>Phe<br>460 | CAA<br>Gln | GAC<br>Asp | TAC<br>Tyr | ATT<br>Ile | AAG<br>lys<br>465 | TCC<br>Ser | TAT<br>Tyr | TTG<br>Leu | GAA<br>Glu | CAA<br>Gln<br>470 | GCG<br>Ala | AGT<br>Ser | CGG<br>Arg | 1443 |
| ATC<br>Ile | TGG<br>Trp<br>475 | TCA<br>Ser | TGG<br>Trp | CTC<br>Leu | CTT<br>Leu | GGG<br>Gly<br>480 | GCG<br>Ala | GCG<br>Ala | ATG<br>Met | GTA<br>Val | GGG<br>Gly<br>485 | GCC<br>Ala | GTC<br>Val | CTC<br>Leu | ACT<br>Thr | 1491 |
| GCC<br>Ala<br>490 | CTG<br>Leu | CTG<br>Leu | GCA<br>Ala | GGG<br>Gly | CTT<br>Leu<br>495 | GTG<br>Val | AGC<br>Ser | TTG<br>Leu | CTG<br>Leu | TGT<br>Cys<br>500 | CGT<br>Arg | CAC<br>His | AAG<br>Lys | AGA<br>Arg | AAG<br>Lys<br>505 | 1539 |
| CAG<br>Gln | CTT<br>Leu | CCT<br>Pro | GAA<br>Glu | GAA<br>Glu<br>510 | AAG<br>Lys | CAG<br>Gln | CCA<br>Pro | CTC<br>Leu | CTC<br>Leu<br>515 | ATG<br>Met | GAG<br>Glu | AAA<br>Lys | GAG<br>Glu | GAT<br>Asp<br>520 | TAC<br>Tyr | 1587 |
| CAC<br>His | AGC<br>Ser | TTG<br>Leu | TAT<br>Tyr | CAG<br>Gln<br>525 | AGC<br>Ser | CAT<br>His | TTA<br>Leu | TAAAAGGCTT | | AGGCAATAGA | | GTAGGGCCAA | | | | 1641 |
| AAAGCCTGAC | | CTCACTCTAA | | CTCAAAGTAA | | TGTCCAGGTT | | CCCAGAGAAT | | ATCTGCTGGT | | | | | | 1701 |
| ATTTTTCTGT | | AAAGACCATT | | TGCAAAATTG | | TAACCTAATA | | CAAAGTGTAG | | CCTTCTTCCA | | | | | | 1761 |
| ACTCAGGTAG | | AACACACCTG | | TCTTTGTCTT | | GCTGTTTTCA | | CTCAGCCCTT | | TTAACATTTT | | | | | | 1821 |
| CCCCTAAGCC | | CATATGTCTA | | AGGAAAGGAT | | GCTATTTGGT | | AATGAGGAAC | | TGTTATTTGT | | | | | | 1881 |
| ATGTGAATTA | | AAGTGCTCTT | | ATTTT | | | | | | | | | | | | 1906 |

( 2 ) INFORMATION FOR SEQ ID NO: 2:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:2 :

Tyr Met Asn Gly Thr Met Ser Gln Val
                5

( 2 ) INFORMATION FOR SEQ ID NO: 3:

( i ) SEQUENCE CHARACTERISTICS:
        ( A ) LENGTH: 10 amino acids
        ( B ) TYPE: amino acid ( D ) TOPOLOGY: linear ( x i ) SEQUENCE DESCRIPTION: SEQ ID NO:3:

Met Leu Leu Ala Val Leu Tyr Cys Leu Leu
                    5

( 2 ) INFORMATION FOR SEQ ID NO: 4:

( i ) SEQUENCE CHARACTERISTICS:
                ( A ) LENGTH: 9 amino acids
                ( B ) TYPE: amino acid
                ( D ) TOPOLOGY: linear ( x i ) SEQUENCE DESCRIPTION: SEQ ID NO:4:

Met Leu Leu Ala Val Leu Tyr Cys Leu
                    5

( 2 ) INFORMATION FOR SEQ ID NO:5:

( i ) SEQUENCE CHARACTERISTICS:
                ( A ) LENGTH: 9 amino acids
                ( B ) TYPE: amino acid
                ( D ) TOPOLOGY: linear ( x i ) SEQUENCE DESCRIPTION: SEQ ID NO:5:

Leu Leu Ala Val Leu Tyr Cys Leu Leu
                    5

( 2 ) INFORMATION FOR SEQ ID NO:6:

( i ) SEQUENCE CHARACTERISTICS:
                ( A ) LENGTH: 10 amino acids
                ( B ) TYPE: amino acid
                ( D ) TOPOLOGY: linear ( x i ) SEQUENCE DESCRIPTION: SEQ ID NO:6:

Ser Glu Ile Trp Arg Asp Ile Asp Phe Ala
                    5

( 2 ) INFORMATION FOR SEQ ID NO:7:

( i ) SEQUENCE CHARACTERISTICS:
                ( A ) LENGTH: 9 amino acids
                ( B ) TYPE: amino acid
                ( D ) TOPOLOGY: linear ( x i ) SEQUENCE DESCRIPTION: SEQ ID NO:7:

Ser Glu Ile Trp Arg Asp Ile Asp Phe
                    5

( 2 ) INFORMATION FOR SEQ ID NO:8:

( i ) SEQUENCE CHARACTERISTICS:
                ( A ) LENGTH: 9 amino acids
                ( B ) TYPE: amino acid
                ( D ) TOPOLOGY: linear ( x i ) SEQUENCE DESCRIPTION: SEQ ID NO:8:

Glu Ile Trp Arg Asp Ile Asp Phe Ala
                    5

( 2 ) INFORMATION FOR SEQ ID NO:9:

( i ) SEQUENCE CHARACTERISTICS:
                ( A ) LENGTH: 10 amino acids
                ( B ) TYPE: amino acid
                ( D ) TOPOLOGY: linear (xi) SEQUENCE DESCRIPTION: SEQ ID NO:9:

Glu Glu Asn Leu Leu Asp Phe Val Arg Phe
                  5                      10

(2) INFORMATION FOR SEQ ID NO:10:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:10:

Tyr Glu Ile Trp Arg Asp Ile Asp Phe (2) INFORMATION FOR SEQ ID NO:11:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:11:

Glu Glu Lys Leu Ile Val Val Leu Phe
                  5

(2) INFORMATION FOR SEQ ID NO:12:

(i) SEQUENCE CHARACTERISTICS:
        (A) LENGTH: 9 amino acids
        (B) TYPE: amino acid
        (D) TOPOLOGY: linear (ix) FEATURE:
        (D) OTHER INFORMATION: Xaa is any amino acid (xi) SEQUENCE DESCRIPTION: SEQ ID NO:12:

Xaa Glu Ile Trp Arg Asp Ile Asp Phe
                  5